United States Patent
Strohhoefer et al.

(10) Patent No.: US 10,052,422 B2
(45) Date of Patent: Aug. 21, 2018

(54) SYSTEM FOR DETECTING A STATE OF A DIALYZER APPARATUS, AND SENSOR DEVICE WHICH CAN BE USED FOR THIS PURPOSE

(71) Applicant: B. BRAUN AVITUM AG, Melsungen (DE)

(72) Inventors: Christof Strohhoefer, Kassel (DE); Silvie Krause, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 388 days.

(21) Appl. No.: 14/779,271

(22) PCT Filed: Mar. 27, 2014

(86) PCT No.: PCT/EP2014/056212
§ 371 (c)(1),
(2) Date: Sep. 22, 2015

(87) PCT Pub. No.: WO2014/161771
PCT Pub. Date: Oct. 9, 2014

(65) Prior Publication Data
US 2016/0058934 A1    Mar. 3, 2016

(30) Foreign Application Priority Data
Apr. 3, 2013  (DE) .................. 10 2013 103 335

(51) Int. Cl.
*C02F 1/00* (2006.01)
*A61M 1/16* (2006.01)
(Continued)

(52) U.S. Cl.
CPC ....... *A61M 1/1601* (2014.02); *A61B 5/14557* (2013.01); *A61M 1/16* (2013.01);
(Continued)

(58) Field of Classification Search
None
See application file for complete search history.

(56) References Cited

U.S. PATENT DOCUMENTS 3,900,396 A    8/1975  Lamadrid
4,508,622 A    4/1985  Polaschegg et al.
(Continued)

FOREIGN PATENT DOCUMENTS

DE    25 09 640    9/1975
DE    32 23 051    7/1993
(Continued)

OTHER PUBLICATIONS

German Search Report for DE 10 2013 103 335.0 dated Jan. 15, 2014, with translation of p. 3.
International Search Report and Written Opinion for PCT/EP2014/056212 dated Jul. 3, 2014.

*Primary Examiner* — Richard C Gurtowski
(74) *Attorney, Agent, or Firm* — RatnerPrestia

(57) ABSTRACT

A system for acquiring or measuring information relating to a state of dialysance, identifying a dialyzer apparatus, or identifying a membrane filter device during the operation of the dialyzer apparatus in a dialysis treatment of a patient. The dialyzer apparatus includes a housing having an internal volume portion and a membrane filter device arranged within the internal volume portion. The housing allows transmission of radiation. A sensor device connected to the housing of the dialyzer apparatus includes a signal receiving device designed to receive a radiation signal, from the housing, the signal characteristic of the state or the identification of the dialyzer apparatus or of the membrane filter unit of the dialyzer apparatus.

19 Claims, 4 Drawing Sheets

(51) Int. Cl.
  *A61M 1/34* (2006.01)
  *A61M 1/36* (2006.01)
  *A61B 5/1455* (2006.01)
  *G01N 21/27* (2006.01)
  *G01N 29/36* (2006.01)
  *A61B 5/053* (2006.01)
  *A61B 5/145* (2006.01)
  *A61B 5/00* (2006.01)

(52) U.S. Cl.
  CPC ........ *A61M 1/1603* (2014.02); *A61M 1/1605* (2014.02); *A61M 1/34* (2013.01); *A61M 1/3406* (2014.02); *A61M 1/367* (2013.01); *A61M 1/3609* (2014.02); *G01N 21/27* (2013.01); *G01N 29/36* (2013.01); *A61B 5/053* (2013.01); *A61B 5/14535* (2013.01); *A61B 5/14556* (2013.01); *A61B 5/4836* (2013.01); *A61B 2560/0443* (2013.01); *A61B 2562/08* (2013.01); *A61M 2205/3313* (2013.01); *A61M 2205/3317* (2013.01); *A61M 2205/3324* (2013.01); *A61M 2205/3569* (2013.01); *A61M 2205/52* (2013.01); *A61M 2205/60* (2013.01); *A61M 2205/6054* (2013.01); *A61M 2205/6063* (2013.01); *A61M 2205/6072* (2013.01); *A61M 2230/20* (2013.01)

(56) References Cited

U.S. PATENT DOCUMENTS

| | | |
|---|---|---|
| 5,100,554 A | 3/1992 | Polaschegg |
| 8,743,353 B2 | 6/2014 | Bado et al. |
| 2001/0037079 A1 | 11/2001 | Burbank et al. |
| 2004/0067594 A1 | 4/2004 | Mori et al. |
| 2006/0283801 A1 | 12/2006 | Chevallet et al. |
| 2007/0007184 A1 | 1/2007 | Voto et al. |
| 2012/0095351 A1 | 4/2012 | Klose et al. |
| 2012/0154789 A1 | 6/2012 | Barrett et al. |
| 2012/0316799 A1 | 12/2012 | Gagel |
| 2013/0281964 A1 | 10/2013 | Kugelmann et al. |
| 2013/0306543 A1 | 11/2013 | Beisser |

FOREIGN PATENT DOCUMENTS

| | | |
|---|---|---|
| DE | 196 27 595 | 1/1997 |
| DE | 10 2009 036 044 | 2/2011 |
| DE | 10 2010 043574 | 5/2012 |
| DE | 10 2011 106 111 | 12/2012 |
| DE | 10 2012 007 904 | 10/2013 |
| EP | 0 428 927 | 5/1991 |
| EP | 0 504 772 | 9/1992 |
| EP | 0 552 014 | 7/1993 |
| GB | 2 303 082 | 2/1997 |
| WO | WO 98/17193 | 4/1998 |
| WO | WO 02/34314 | 5/2002 |
| WO | WO 2004/056263 | 7/2004 |

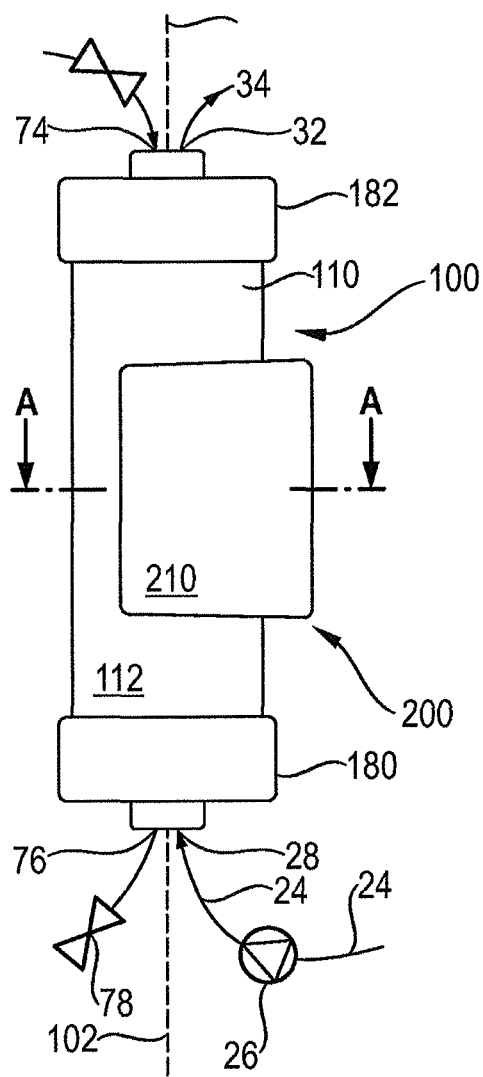
Fig. 2A
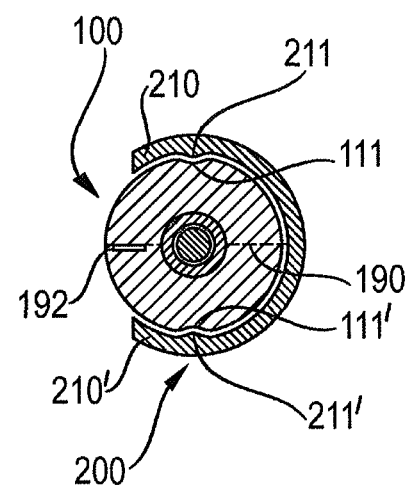
Fig. 2C  A-A
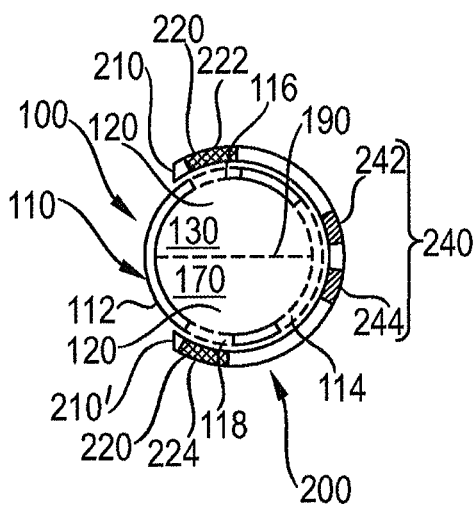
Fig. 2B

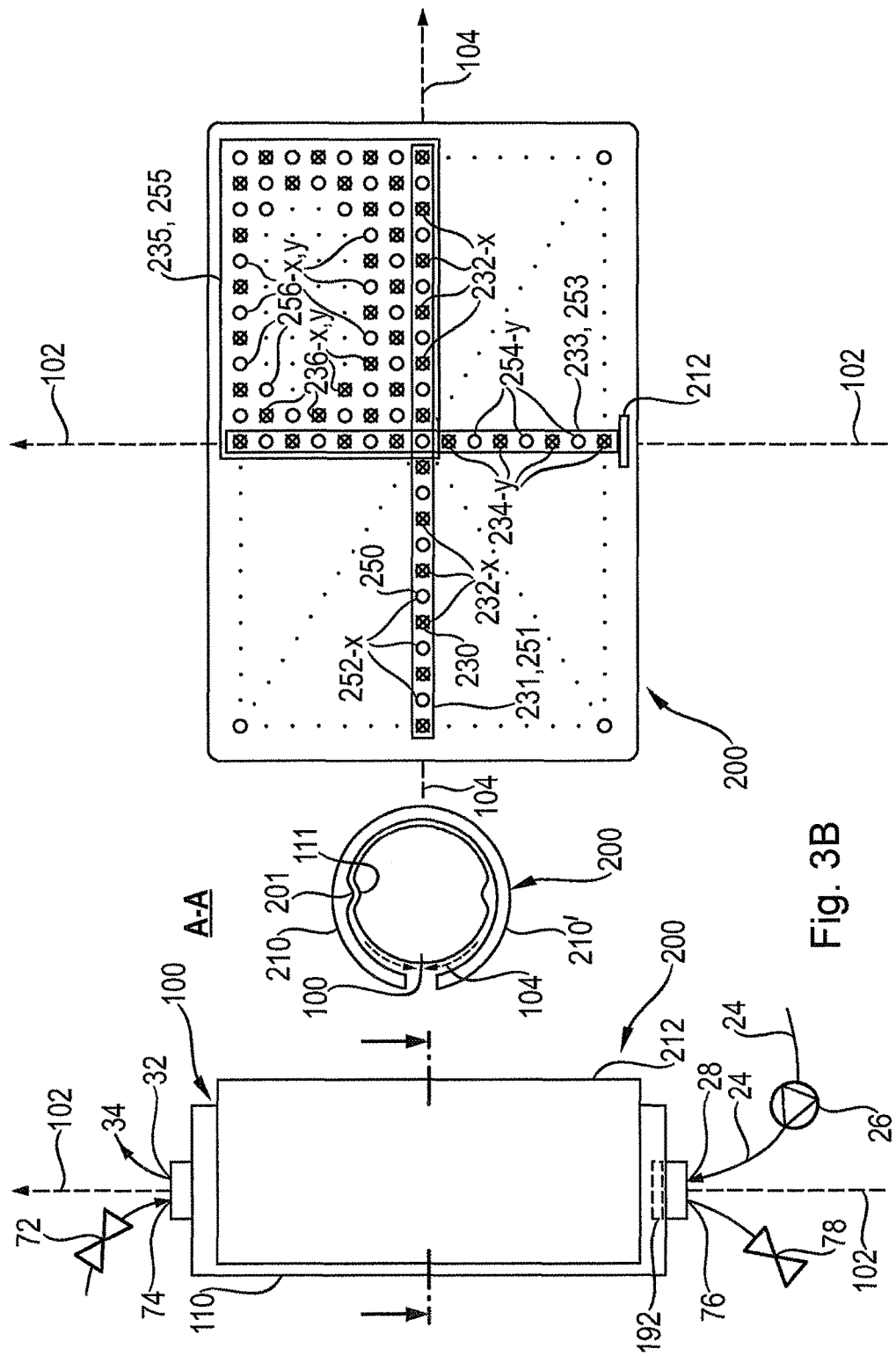

SYSTEM FOR DETECTING A STATE OF A DIALYZER APPARATUS, AND SENSOR DEVICE WHICH CAN BE USED FOR THIS PURPOSE

CROSS REFERENCE TO RELATED APPLICATIONS

This application is the U.S. national phase application of PCT International Application No. PCT/EP2014/056212 filed Mar. 27, 2014, which claims priority to German Patent Application No. DE 10 2013 103 335.0 filed Apr. 3, 2013, the contents of each application being incorporated by reference herein.

FIELD OF THE INVENTION

The invention relates, inter alia, to a system for detecting a state, for example, a dialysance, and, optionally, for identifying a dialyzer apparatus or a component thereof such as, for example, a membrane filter device of the dialyzer apparatus before or during the operation of the dialyzer apparatus, for example, treating a patient's blood. The invention further relates to a sensor device for detecting a state of a dialyzer and, optionally, for identifying a dialyzer, also referred to below as a dialyzer apparatus, or a component thereof such as, for example, a membrane filter device of the dialyzer apparatus; a dialyzer apparatus that is designed for detecting or measuring such information with such a sensor device; a system comprising such a sensor device and such a dialyzer apparatus; as well as a dialysis machine having such a sensor device and such a dialyzer apparatus.

BACKGROUND

In order to place the invention in the context of prior art, we first refer to FIG. 1. FIG. 1 shows a dialysis machine 300 for performing the hemodialysis treatment of a patient 10 in a dialysis operation. Alternatively or additionally, the dialysis machine 300 may also be designed to perform hemofiltration or hemodiafiltration and may also comprise a dialysate flow path or a dialysate fluid circuit 40, hereinafter also referred to as the dialysate circuit 40, a blood flow path or blood circuit 20 located extracorporeally of the patient 10, and a dialyzer apparatus 100 having an internal volume portion 120 and a membrane filter device 190 located therein having a membrane. The dialyzer apparatus 100 treats the blood of the patient 10, for example, via a hemodialysis treatment because the exchange of materials between the blood of the patient 10 flowing through the blood circuit 20 and the dialysate flowing through the dialysate circuit 40 occurs therein or in the membrane disposed therein. Here and in the text below, the term "dialysate" is intended to refer to the dialysate liquid and/or to the dialysate liquid used.

The membrane of the membrane filter device 190 spatially separates the internal volume portion 120 to form the blood region 130 through which the blood of the patient 10 flows and the dialysate region 170 through which the dialysate flows. The exchange of materials through the membrane includes the passage of substances normally excreted with urine, some of them toxic, through the membrane into the dialysate caused by a concentration gradient in the blood of said substances and, vice versa, the passage of substances dissolved in the prepared dialysate through the membrane and into the blood of the patient caused by a concentration gradient of said substances in the dialysate. The substances contained in the prepared dialysate are added to and dissolved in the dialysate via components 42, 44, 54 of the dialysate preparation in a distribution of concentrations specifically prepared for the patient 10.

Devices are known with which measurements of parameters may be made outside of the dialyzer apparatus 100, from which conclusions may be drawn regarding the performance, for example, the dialysance, of the dialyzer apparatus or the clearance of the extracorporeal blood circuit. Corresponding methods for analyzing the parameters measured by said devices and for providing information regarding the performance of a dialyzer apparatus are also known.

DESCRIPTION OF THE RELATED ART

DE 32 23 051 A1 discloses a dialyzer apparatus having a regulated dialysate composition, with the material composition of the dialysate being determined on the basis of signals from sensors located upstream and downstream of the dialysate region in the dialysate circuit for the measurement of electrical conductivity. On the basis of the device disclosed in DE 32 23 051 A1, a method disclosed in EP 428 927 A1 may be used to determine dialysance based on a variation in the composition of the dialysate liquid. The numeric value obtained for the dialysance of the dialyzer using this method is identical to that of the clearance that shows the quantity of, for example, toxic substances, removed from the blood per unit of time.

DE 10 2010 043 574 A1 discloses a manually opened clamp mounting to be attached in a removable fashion to a single-use medical article such as, for example, a line or a tube of the blood circuit 20 or a dialyzer 100 designed as a single-use article. The clamp mounting comprises a first clamping jaw and a second clamping jaw hinged thereon and pivotable relative to the first clamping jaw, between which the single-use article to be attached may be clamped, and a sensor for detecting the relative position of the clamping jaws. Based on the signal generated by the sensor, the relative position of the clamping jaws and therefore the size and/or diameter of the object clamped between the clamping jaws may be determined. Based on this, the type of object held in the clamp may be determined.

US 2012/0154789 A1 describes a sensor clip unit for the optical monitoring of blood flowing through a blood chamber connected in-line to a blood duct, in particular for the monitoring of materials dissolved in the blood. The sensor clip unit comprises two clamping jaws pivotable relative to one another and disposed opposite one another relative to the blood chamber, between which the blood chamber may be clamped. A light emitter is disposed in the first clamping jaw and a photodetector is disposed in the second clamping jaw. The photodetector measures the intensity of light with wavelengths in the infrared spectral range that has passed through the blood flowing through the blood chamber. The wavelengths are selected in a material-specific fashion such that the absorption of light by specific materials contained in the flowing blood such as, for example, hematocrit or oxygen, is measured and variations in the blood volume may be determined.

SUMMARY OF THE INVENTION

The invention is based, inter alia, on the insight that a contact-free measurement of information and/or parameters with regard to the liquids flowing through a dialyzer (dialysate and/or blood) and/or measurement for the purpose of identification, for example, of a type of dialyzer apparatus and/or membrane filter device present in the dialyzer apparatus, is advantageous. Using exemplary embodiments of the invention, measurements may be performed or an identification may be conducted directly on the dialyzer. This is advantageous because the dialyzer represents the most critical part of a dialysis machine from a therapeutic viewpoint because the material exchange takes place in the dialyzer and the efficiency of the dialysis is substantially influenced there. Also, for reasons of geometry, the blood in the dialyzer is in a highly mutual interaction with the membrane of the membrane filter device, such that the strongest effects on the parameters relating to blood and dialysate take place in the dialyzer. Here, it is also possible to take into account that parameters indicative of dialysis efficiency, for example, hematocrit and blood coagulation properties, can also change over the time the blood is in the dialyzer and return to their original state outside of the dialyzer via compensation mechanisms. For example, due to the pressure conditions in modern dialyzers that are optimized for a high flow rate, hematocrit will initially increase and then decrease over the length of the blood region. This trend in the hematocrit concentrations in a dialyzer could not be directly measured up to now even though it is known that maximum hematocrit concentration is a decisive parameter for coagulation, clotting, and hemolytic effects. Local concentrations and differences in concentration of the materials dissolved in the dialysate also contain important information regarding the quality of the hemopurification in the dialyzer along the length of the membrane. A measurement and/or monitoring of corresponding parameters in the exemplary embodiments such as, for example, the coagulation state, conducted directly on the dialyzer is therefore advantageous.

The invention attains the object of creating a reusable sensor device and/or a system having a reusable sensor device that allows the most direct information possible regarding the state of and/or the identification of a dialyzer apparatus embodied as a single-use article or a membrane filter device embodied as a single-use article of the dialyzer apparatus to be measured directly at the dialyzer apparatus.

According to one or more embodiments, a device for the measurement of parameters is provided from which information regarding the identification of a dialyzer apparatus or a membrane filter device of the dialyzer apparatus may be obtained during its operation in a dialysis treatment of the patient. Here, the measurements are conducted directly at the dialyzer apparatus. The dialyzer apparatus and/or at least the membrane filter device placed therein is a single-use product that, as a rule, is used only during a single dialysis treatment on one patient and is disposed of thereafter. For this reason, it is advantageous for the sensor device to be reusable for multiple dialyzer apparatuses.

The invention provides a system having a dialyzer apparatus and a sensor device, a sensor device, a dialyzer apparatus, and a dialysis machine having the features of the independent claims. Further advantageous refinements are the subject matter of the subordinate claims.

According to a first aspect of the invention, a sensor device as well as a system for detecting or measuring information for the identification of a dialyzer apparatus or a membrane filter device of the dialyzer apparatus before and/or during operation of the dialyzer apparatus in a dialysis treatment of a patient is provided. In one or more exemplary embodiments, the system comprises a dialyzer apparatus having a housing surrounding an internal volume portion and a membrane filter device essentially disposed in the internal volume portion, and a sensor device that may be operatively connected to the housing of the dialyzer apparatus in a detachable fashion and that comprises a signal receiving unit that is designed to receive at least one single such as, for example, a radiation signal, for example, from the surface of the housing, from an identifier attached to or embodied on the surface of the housing such as a label, or from the internal volume portion of the housing, said signal being characteristic of the state and/or the identification of the dialyzer apparatus and/or the membrane filter device of the dialyzer apparatus. The housing may optionally be permeable at least in some areas to a signal, for example, a radiation signal, in order to, for example, be able to identify materials, substances, or markings in the interior of the housing. An identification of the dialyzer or components thereof may alternatively or additionally be accomplished with features attached to the outside of the housing.

According to a second aspect of the invention, a sensor device is provided that is designed to be operatively attachable to the housing of the dialyzer apparatus in a removable fashion; when connected to the dialyzer apparatus, a system may be formed according to the first aspect of the invention.

According to a third aspect of the invention, a dialyzer apparatus, i.e., preferably a dialyzer, having a housing surrounding an internal volume portion and the membrane filter device essentially disposed in the internal volume portion is provided, with the housing being permeable at least in some areas to a signal such as, for example, a radiation signal. Here, the dialyzer apparatus may be designed in such a way that is sensor device according to the second aspect of the invention may be operatively connected to it in a detachable fashion and, when connected, is able to form a system according to the first aspect of the invention.

According to a fourth aspect of the invention, a dialysis machine is provided for conducting dialysis treatment on a patient. The dialysis machine comprises a dialyzer apparatus according to the third aspect of the invention and the sensor device according to the second aspect of the invention, whereby a system may be formed according to the first aspect of the invention. The sensor device may be operatively connected to such a system in a detachable fashion.

The design of the sensor device to be operatively connectable in a detachable fashion to the dialyzer apparatus allows the sensor device to be used repeatedly and/or on a plurality of dialyzer apparatuses to measure information, while the dialyzer apparatus or parts thereof may be designed as single-use articles.

The ability of the sensor device to directly connect to the dialyzer apparatus, i.e., to the dialyzer, allows the measurement of information to be conducted directly at the dialyzer apparatus and thus for the desired information to be measured in the most direct and/or detailed manner possible.

The sensor device according to aspects of the invention allows the identification of the dialyzer apparatus or the membrane filter device of the dialyzer apparatus to be conducted in a direct, error-free, and reliable fashion and for information regarding the state of the dialyzer apparatus, in particular the state of the membrane filter device, to be measured in a precise, detailed, and direct fashion at the dialyzer apparatus and/or the membrane filter device. Such information may include parameters that are indicative of the efficiency of the material exchange for the membrane of the membrane filter device, particularly including dialysance. The efficiency of the material exchange is a function of the material composition of the prepared dialysate, the material composition, in particular the concentration of materials contained in the patient's blood to be removed from the patient's blood via dialysis treatment, and of processes in the dialyzer apparatus, in particular on the capillary level and/or in the pores of the membrane of the membrane filter device, such as, for example, a localized clog in the membrane due to, for example, clotting in the filter. The signal to be measured may be selected in such a way that it is indicative of at least one of these values. This allows the possibility of a space-resolved measurement of parameters in the dialyzer. This measurement may occur simultaneously or sequentially at two or more points on or in the dialyzer, for example, along the dialyzer in its axial direction, along its circumference, or also obliquely thereto, for example, along one or more lines, or at locations distributed in any other desired fashion, or even at multiple sequential measuring points located at least partially in the radial direction of the dialyzer.

The system according to the first aspect of the invention may be designed to provide the measured signal to an analysis unit that, based on the measured signal, identifies or at least is able to identify the dialyzer apparatus and, optionally, additionally generates data that can be used to control operating parameters of a dialysis machine according to the fourth aspect of the invention.

The signal receiving unit may be designed to detect radiation signals of any kind or even selected from a group including, for example, the following: a) electromagnetic radiation with any desired wavelength, for example, in the optical range such as far infrared (FIR), infrared (IR), near infrared, visible, and ultraviolet (UV) light, b) electromagnetic radiation having a wavelength or a wavelength range or the corresponding frequency range from the entire electromagnetic spectrum such as, for example, in the microwave range, in the terahertz range, i.e., in the submillimeter range, or in the range of radio waves, such as radio waves used in RFID technology, and c) ultrasound waves. The wide range of options for the signal receiving unit allows different information and/or types of information and/or various parameters of the dialyzer apparatus or the membrane filter device to be measured.

The signal receiving unit may comprise a receiver for a magnetic, electrical, or electromagnetic signal, said signal being indicative of a capacity to be measured and/or an inductivity to be measured that is characteristic of the state and/or the identification of the dialyzer apparatus and/or the membrane filter device. Such signal may, for example, be detected in a reliable and error-free manner from the exterior region or even from the edge or internal volume portion of the dialyzer apparatus by the receiver located, for example, on or outside the dialyzer apparatus.

Each of the embodiments of the signal receiving unit described above and the measurements of information that may be made thereby may be considered a separate invention for which a divisional application may optionally be filed.

The sensor device according to the second aspect of the invention may comprise a radiation transmitting unit that is designed to emit radiation, in particular radiation from the entire electromagnetic spectrum such as, for example, radiation with a wavelength or a wavelength range or the corresponding frequency range from the entire electromagnetic spectrum such as, for example, microwave range, terahertz range, i.e., in the submillimeter range, or in the range of radio waves such as, for example, radio waves used in RFID technology, or optical radiation, or ultrasound radiation, onto the housing or even into the internal volume portion of the housing of the dialyzer apparatus. Correspondingly, the signal receiving unit may be designed to measure the intensity of radiation emitted by the radiation transmitting unit. Thus, in operation, the measured radiation may be the result of an interaction characteristic of the state of the dialyzer apparatus that has taken place in the internal volume portion of the housing between the radiation and one or more of the following: the dialysate and/or the blood, a substance contained in the dialysate and/or the blood, the membrane filter device and a substance held in and/or on the membrane filter device that or originates from the blood and/or the dialysate. Thus, at least part of the measured radiation from the internal volume portion is able to arrive at the signal receiving unit. In particular, the interaction can be triggered by the radiation emitted into the internal volume portion by the radiation transmitting unit. The measurement of a result of an electromagnetic, for example, optical, interaction of, for example, radiation emitted into the internal volume portion, allows for the touch-free measurement of the above-mentioned elements, for example, present in the internal volume portion during operation and thus the measurement of parameters directly characterizing the state of the dialyzer apparatus. In measuring radiation originating, for example, from the surface or from the interior of the dialyzer and received as a reflection, diffusion, diffraction, or frequency conversion of electromagnetic radiation such as light that is diffuse or emitted in a targeted fashion, it is possible for a space-resolved measurement to be conducted in one, multiple, or all exemplary embodiments. Space-resolved measurements allow, for example, the space-resolved determination of dialyzer-specific properties. The use of spatial resolution as a measurement principle allows, for example, influences such as diffraction or deflection of an incident light beam to be determined and parameters to be derived therefrom. For spatial resolution, for example, measurements may be taken at one or more positions such that dialyzer-specific properties may be measured in a space-resolved fashion. Here, the plurality of measurements may be combined with one another in order to increase measurement accuracy. To this end, the measured radiation may be detected at multiple points in the direction of the beam path, or transversely or obliquely thereto, by one or more sensors. Thus, spatial resolution results as a measurement principle, for example, for determining the diffraction of an incident electromagnetic ray, such as light, and for driving parameters therefrom, for example, regarding the index of refraction, the internal structure, the material of the dialyzer, or the like.

An electromagnetic, for example, optical, interaction may be triggered that is selected, for example, from a group comprising following:

reflection of radiation on the surface of the housing or reflection of electromagnetic, for example, optical, radiation emitted by the radiation transmitting unit on a boundary surface between the housing wall, for example, the window region, and the dialysate or the blood, reflection of radiation emitted by the radiation transmitting unit on a boundary surface between the membrane filter device and the dialysate or the blood, transmission of radiation emitted by the radiation transmitting unit having a measuring wavelength that can be absorbed by a substance contained in the dialysate and/or in the blood and that, on its way to the radiation receiving unit, has followed a beam path through the dialysate and/or through the blood, emission of luminescent or fluorescent radiation by a material contained in the dialysate and/or in the blood, with a luminescent or fluorescent reaction in said material being triggered by the radiation emitted by the radiation transmitting unit, refraction of the radiation emitted by the radiation transmitting unit onto a boundary surface between the housing wall, for example, a window region, and the dialysate or the blood, with the transmitted radiation striking the boundary surface at an angle of incidence between 0° and 90°, scattering of the radiation emitted by the radiation transmitting unit on a substance contained in the dialysate or in the blood, including dynamic scattering of monochromatic laser radiation, interaction of the radiation emitted by the radiation transmitting unit with an identification unit attached to the dialyzer apparatus or the membrane filter device such as, for example, a barcode, an RFID code, or a color code field that comprises an identifying feature characteristic for the identification of the dialyzer apparatus, a component thereof, a medium present in or flowing through the dialyzer apparatus, or the membrane filter device. Any codes may be used for this purpose such as, for example, optical; acoustic, electrical, magnetic, and other codes, including a mechanical form of encoding, for example, a special housing shape that is simultaneously an optical element, or text recognition,

RFID.

The highly versatile selection possibilities of the optical interaction that the measured radiation in the internal volume portion has with the elements located therein allows different information or types of information or various parameters for the identification of the dialyzer or for detecting elements present in the internal volume portion or the membrane filter device to be measured.

In one exemplary embodiment, multiple exemplary embodiments, or all exemplary embodiments, the dialyzer apparatus or the membrane filter device comprise a so-called passive identification unit comprising an identification feature that is characteristic for the identification of the dialyzer apparatus or the membrane filter device that may be read, for example, by illuminating the identification unit with a predetermined electromagnetic radiation. Here, the sensor device may comprise a radiation transmitting unit that is designed to emit the predetermined electromagnetic radiation, in particular onto the identification unit. Here, the signal receiving unit may comprise an identification reader unit that is designed to detect a parameter of the radiation that is indicative of the identifying feature and to determine the identifying feature. In this embodiment, the identification unit may be, for example, a barcode, a color code field, or a passive RFID chip. The identification unit allows information regarding the identification of the dialyzer apparatus or the membrane filter device to be measured in a particularly reliable, direct, and essentially error-and malfunction-free manner.

Alternatively, the dialyzer apparatus or the membrane filter device may comprise a so-called active identification unit that is able to transmit electromagnetic radiation having an identifying feature that is characteristic for the identification of the dialyzer apparatus or the membrane filter device. In such a case, the signal receiving unit may comprise an identification reader unit that is designed to detect the electromagnetic radiation emitted by the identification unit and to determine the identifying feature, for example, after a demodulation analysis. Such an identification unit may, for example, be an active RFID chip. In this embodiment with an active identification unit, it is also possible for information regarding the identification of the dialyzer apparatus or the membrane filter device to be measured in a particularly reliable, direct, and essentially error-and malfunction-free manner.

The radiation transmitting unit may comprise at least one or more of the following features: a light source that emits light in a narrow-band spectral range, such as a laser or an LED, a light conductor that guides light emitted by a light source emitting light in a narrow-band spectral range, and an uncoupling section from which the light exits, a light source that emits light in a wide-band spectral range, such as a halogen lamp, or a light conductor that guides light emitted by a light source emitting light in a wide-band spectral range, and an uncoupling section from which the light exits. This broad range of configuration options for the radiation transmitting unit allows for different types of optical interactions to be induced of the radiation transmitted into the internal volume portion with the elements present therein and, as a result, for different parameters and/or data regarding the status of the dialyzer apparatus and/or the membrane filter device to be measurable.

The radiation transmitting unit may comprise a one-dimensional arrangement or a two-dimensional arrangement of multiple radiation emission areas. The radiation transmitting unit may comprise one or more transmitters or emitters and, optionally, light conductors as well. In one or more exemplary embodiments, the housing itself may serve as a light conductor. An excellent alignment, i.e., a preferred, for example, a linear alignment, of the one-dimensional or two-dimensional arrangement in operation and in the connected state of the sensor device and the dialyzer apparatus essentially parallel to a flow direction of the dialysate in the dialysate region, or parallel to the flow direction of the blood in the blood region, or parallel to a longitudinal axis of the dialyzer apparatus, or along the circumference of the housing, or transverse or oblique to these alignments, or combined two or more of these alignments, i.e., distributed in a two-dimensional or three-dimensional fashion, may be aligned. The structure of the radiation transmitting unit with a one-or two-dimensional arrangement of a plurality of light-emitting regions allows the emitted light to be spatially distributed and to be emitted into the internal volume portion of the dialyzer apparatus in a spatially selectively distributed fashion and, as a result, for example, in the case of a suitable design of the radiation measurement unit, allows the desired information to be measured in a spatially selective fashion.

The sensor device may comprise a radiation measurement unit, for example, having a radiation influencing unit such as an optical measuring unit, and a radiation detector, for example, a light detector, having a radiation-or light-sensitive detector surface. The functionality of the radiation influencing unit may also be provided by the housing itself. The housing may, for example, be equipped with one or more light conductors.

The radiation influencing unit or optical measuring unit may optionally have a focal depth and/or a focal direction. The radiation influencing unit may also be designed to project or focus radiation or light from the light source at a certain point in the dialyzer. Alternatively or additionally, the radiation influencing unit may be used to focus light from the dialyzer onto the sensor device (detector) and not only to project it. Here, the radiation influencing unit may be designed, like the optical measuring unit, to project a spatial region from the internal volume portion of the housing of the dialyzer apparatus onto the detector surface of the light detector, said spatial region being defined by the focal depth and focal direction. The radiation influencing unit may be designed in such a way that its focal depth and focal direction may be selected so as to select the projected spatial region in the area of the internal volume portion. By this design of the radiation measurement unit, the desired information may be measured in a spatially selective fashion on the outer or edge region or, in some cases, from or in the internal volume portion, for example, to identify the dialyzer.

The sensor device may comprise a radiation measurement unit having at least one radiation inlet region and at least one radiation detector, for example, a light detector, that is designed to detect radiation, such as light, that has entered the at least one radiation inlet region and that is selected, for example, from a group that may include the following: a photodiode, a phototransistor, a CMOS light detector, a photomultiplier having one or more multiplier elements disposed one dimensionally in a linear fashion or distributed in a flat two-dimensional fashion, an avalanche photodiode having one or more of photodiode elements disposed one-dimensionally in a linear fashion or distributed in a flat two-dimensional fashion, a one-dimensional or two-dimensional CCD sensor, and a one-dimensional arrangement or a two-dimensional arrangement of a plurality of photodiodes, phototransistors, CMOS light detectors, photomultipliers, or avalanche photodiodes, or other detectors such as MPPCs (multi-photon pixel counters), or other sensor elements. The multitude of options for selecting the type of radiation detector allows optimally suitable radiation detectors to be provided in each case for the measurement of different parameters and/or information.

A given radiation inlet region may comprise a coupling-in region for an optical light guide or a light-conducting fiber that is designed to direct the radiation to a light detector associated with the radiation inlet region. This design allows the radiation inlet region and the light detector associated therewith to be located at a spatial distance from one another and/or to be spatially decoupled. Thus, light detectors may optionally also be used that occupy a relatively large amount of space to measure light that is "captured" at the radiation inlet region directly on the dialyzer apparatus.

The sensor device may comprise a radiation measurement unit having at least one light detector and a wavelength selection unit such as, for example, a monochromator, with the wavelength selection unit being designed to select a narrow-band wavelength range that includes a reference wavelength from, for example, a wider-band wavelength range of the radiation emitted by the radiation transmitting device, for example, light, in such a way that an optical interaction such as absorption or excitation of luminescent or fluorescent emissions, occurs with a selected material that is located in the internal volume portion of the housing during operation. This material may be, for example, a component of the dialysate and/or the blood. The wave-selective measurement of radiation, for example, light, allowed by this design also allows material-specific measurement.

The Applicant reserves the right to file a separate intellectual property rights application and/or patent application, in particular a divisional application, based on the above description of the sensor device with the various types of radiation transmitting units and radiation measurement units and the optical interactions that may be induced thereby and the measurements of data that may be conducted thereby regarding the state of the dialyzer apparatus or the membrane filter device.

The sensor device may be designed for a task that includes at least one of the following tasks: in the blood region of the internal volume portion, measuring for a parameter indicative of the concentration of a uremic toxin such as the absorption of light having a measured wavelength that is absorbed by the uremic toxin; in the dialysate region of the internal volume portion, measuring for a parameter indicative of the concentration of a uremic toxin such as the absorption of light having a measured wavelength that is absorbed by the uremic toxin; and, in the blood region, measurement of a parameter that is indicative of a physical property of the blood such as, for example, viscosity or hematocrit concentration. The possibility of designing the sensor device for the varied tasks listed above allows for parameters to be measured that are frequently used in practice and/or designate the progress of dialysis therapy on the patient. Correspondingly, on the basis of the measurement of these parameters, the settings and/or operating parameters of a dialysis machine may be adapted over the course of dialysis therapy to the progression of the dialysis therapy.

The housing of the dialyzer apparatus according to the third aspect of the invention may be designed in such a way that the sensor device may be detachably fixed in one or more predetermined positions relative to the housing with a positive fit. In an advantageous embodiment, the housing may comprise coupling regions on its exterior in one or more positions and the sensor device may comprise a second coupling region that is designed to engage with the first coupling region in a positive fit, for example, such that it may be pressed on. The attachment of the sensor device at a predetermined position relative to the housing allows one sensor device to be used with various dialyzer apparatuses to measure the desired information in a reliable fashion under comparable measuring conditions, thus measuring in a comparable fashion.

The sensor device according to the second aspect of the invention is preferably designed in a reusable fashion. Due to this reusability, it becomes efficient and cost-effective to use even relatively elaborate, complex, and therefore expensive sensor equipment.

The design of the sensor device according to the second aspect of the invention to be attachable to the housing of the dialyzer apparatus in a detachable fashion, particularly in a detachable fashion with a positive fit, according to the third aspect of the invention may, for example, be achieved using at least one of the following mechanisms:

the sensor device is designed as a clip device having at least one or more clip cuffs, said clip cuffs being designed to encompass the housing in an angular range of more than 180°, preferably more than 270°, and even more preferably more than 320°, the sensor device comprises a base body and a clip unit having at least one arm or, for example, two or more arms such as a pair of clip arms attached to the base body in an elastically flexible fashion, for example, in an articulated fashion, designed to encompass the housing between themselves and, due to their flexible elastic design or articulation, encompass the housing in the manner of a clip, the sensor device comprises a first member of a connector unit, such as, for example, a dovetail unit, a screw and/or a Velcro fastener, and the dialyzer unit comprises a second member of the connector unit such as, for example, a dovetail mount, a bore or screw thread for screwing in the screw and/or the matching piece to the Velcro fastener, with the first member being designed to engage in a positive fashion with the second member or with the second member being designed to engage in a positive fashion with the first member, and with both parts of the Velcro fastener and/or the other connector units also both being attachable to the "clip," which then fixes the dialyzer apparatus in place by correspondingly tightening the connector unit, the sensor device is clamped into place on the housing with an elastic clamping unit, such as a rubber ring, with the clamping unit being designed to encompass the sensor device and the housing of the dialyzer apparatus in an elastically tense state, the sensor device comprises a base body and at least one pair of arms and/or cuffs articulated on the base body or attached to the base body in an elastically flexible fashion, each of which comprises a distal end region having a first member of a hook or engaging unit, with the arms and/or cuffs being designed to encompass the housing in an angular range of more than 180°, preferably more than 270°, and more preferably more than 320°, and an elastically tensible clamping unit having two end sections located opposite one another on each of which a second hook or engaging unit is provided that is designed to engage in a detachable fashion with a first member of the hook or engaging unit, with each second member on the end section of the clamping unit being able to engage with a first member on the end region of the arms and/or cuffs of the sensor device when the clamping unit is in an elastically tense state, and the sensor device is designed to be integrated in a detachable fashion into the wall of the housing of the dialyzer apparatus, for example, in a recess.

The housing of the dialyzer apparatus according to the third aspect of the invention may comprise a housing wall having at least one window region that is permeable for a signal. The design with a window region that is particularly permeable to a signal allows for precise measurements of the desired information and/or parameters to be conducted using the sensor device to be attached on or in the vicinity of the window region, even in the case of a housing whose housing wall may otherwise be made of a material that is less permeable to the signal, for example, for reasons of cost.

The housing wall may essentially be designed in the shape of the cylinder. This design allows the sensor device to be easily attached in various positions along a longitudinal direction of the housing wall and with lines of sight that vary azimuthally relative to the longitudinal axis.

In a first embodiment, the membrane filter device may be incorporated into the housing of the dilator device in a removable fashion. This embodiment allows for only the membrane filter device to be designed as a single-use article, while the housing of the dialyzer apparatus, in particular, for example, if relatively expensive window regions are integrated therein, may be reusable.

In a second, alternate embodiment, the dialyzer apparatus may additionally comprise another inner housing that may be fixed in the housing in a removable fashion and that essentially encompasses the membrane filter device. Here, the inner housing, in particular with the membrane filter device disposed therein, may be inserted in the housing of the dialyzer apparatus in a removable fashion. This embodiment allows the inner housing with the membrane filter device to be designed as a single-use article, while the housing of the dialyzer apparatus, in particular, for example, if relatively expensive window regions are integrated therein, may be reusable.

In the first embodiment of the dialyzer apparatus, at least the membrane filter device may be designed as a single-use article. In the second embodiment, the inner housing and a membrane filter device may be designed as single-use articles. In this embodiment, in one or more exemplary embodiments, the sensor equipment may also be directly incorporated into the dialyzer housing, with only the electrical interfaces having exterior contact on the dialyzer.

In the first and second embodiments mentioned above, it is preferred for the housing to be designed in such a way that it may be easily and thoroughly cleaned.

The dialyzer apparatus as a whole may also be designed as a single-use article. In this embodiment, it is not necessary to clean the dialyzer apparatus or components thereof after dialysis therapy has been performed on a patient.

The Applicant reserves the right to file a separate intellectual property rights application and/or patent application, in particular a divisional application, based on the above description of the sensor device attachable in a positive-fitting and detachable manner and the various mechanical and/or structural designs of the dialyzer apparatus and the advantages are obtainable therewith.

The internal volume portion of the dialyzer apparatus may comprise a dialysate region through which dialysate may flow during operation and a blood region through which blood may flow during operation, with the dialysate region being spatially separated from the blood region by the membrane filter device. The membrane filter device may be designed to allow a material exchange between the blood and dialysate during operation driven by concentration gradients of materials dissolved in the blood and/or in the dialysate. These designs allow the use of the dialyzer apparatus according to the third aspect of the invention in conventional dialysis machines.

The dialyzer apparatus or a dialysis machine according to the fourth aspect of the invention may comprise at least one housing holder that is designed to be at least mechanically connected to the dialysis machine during operation and to attach the dialyzer apparatus to the dialysis machine in a removable fashion. The housing holder can hold the dialysis device, optionally with the sensor device attached to the dialyzer apparatus in operation, in a reliable fashion.

In the dialysis machine according to the fourth aspect of the invention, the sensor device according to the second aspect of the invention may be integrated into the housing holder. This design simplifies handling of the sensor device because it need not be attached to the housing of the dialyzer apparatus in an additional step.

BRIEF DESCRIPTION OF THE DRAWINGS

The invention is best understood from the following detailed description when read in connection with the accompanying drawings. Included in the drawings are the following figures:

FIG. 2A is a schematic side view of a system having a first embodiment of the sensor device operatively connected in a detachable fashion to a first embodiment of a dialyzer apparatus; FIG. 2B is a schematic top view of the system with the sensor device and the dialyzer apparatus from the left-hand side; and FIG. 2C is a schematic cross-section along the line A-A through the system with the sensor device and the dialyzer apparatus from the left-hand region;

FIG. 3A is a schematic side view of the system having a second embodiment of a sensor device operatively connected in a detachable fashion to a second embodiment of the dialyzer apparatus; FIG. 3B is a schematic cross-section along the line A-A through the system with the sensor device and the dialyzer apparatus from the left-hand region; and FIG. 3C is a schematic depiction of the sensor device from the left-hand region in a rolled-apart state.

DETAILED DESCRIPTION OF THE PREFERRED EMBODIMENTS

Figure 1:
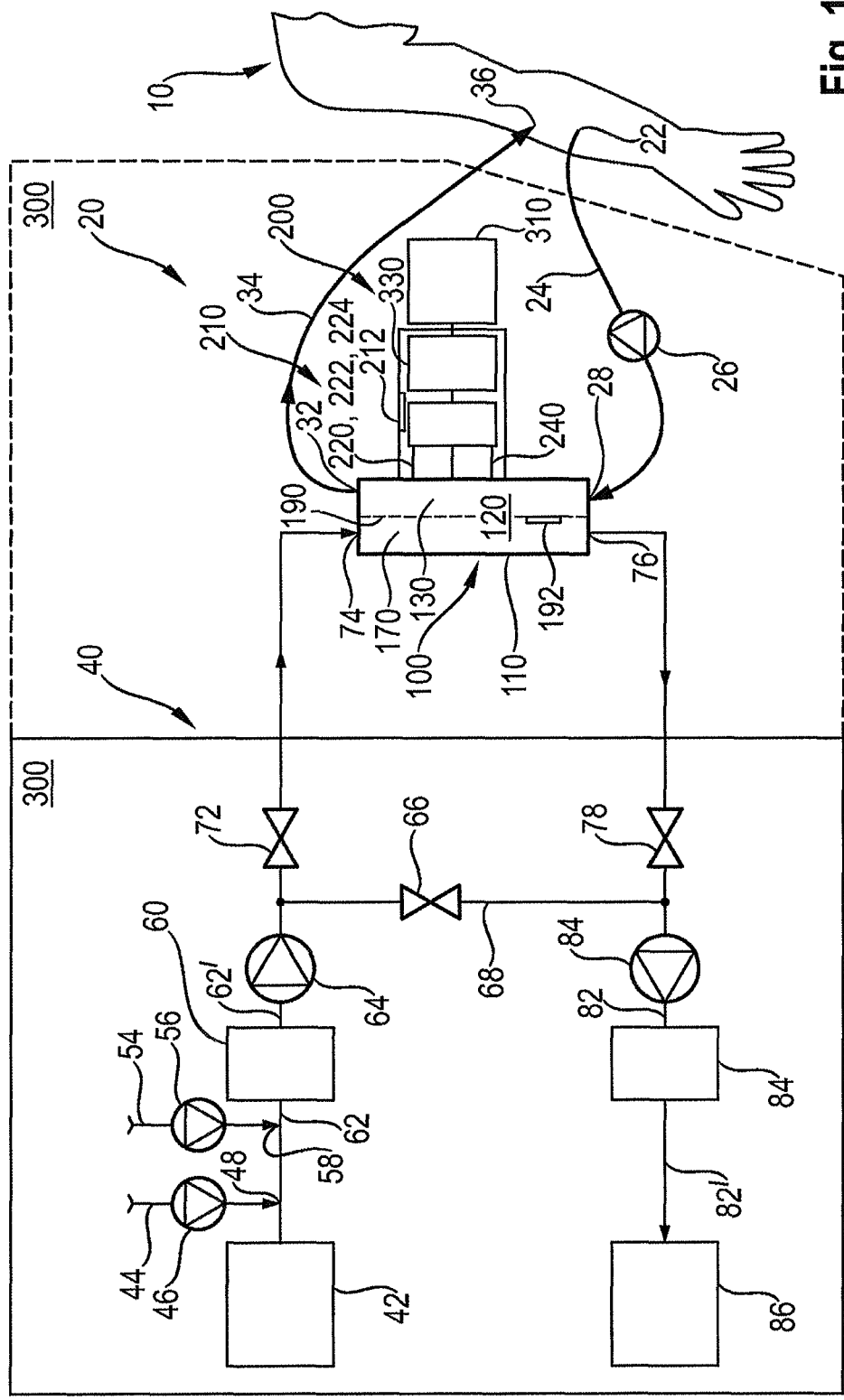
FIG. 1 is a schematic depiction of a blood circuit and a dialysis circuit, for example, disposed in a dialysis machine, during dialysis operation, with a patient being connected to the blood circuit as an extracorporeal blood circuit.

FIG. 1 schematically shows a dialysis machine 300 for conducting a hemodialysis treatment of a patient 10. As already mentioned at the outset, the dialysis machine 300 comprises the dialysate circuit 40, the blood circuit 20, which is extracorporeal to the patient 10, and a dialyzer, i.e., the dialyzer apparatus 100 having the internal volume portion 120 and the membrane filter device 190 disposed therein with the membrane at which the material exchange occurs between the blood of the patient 10 passing through the blood circuit 20 and the dialysate passing through the dialysate circuit 40.

The dialysate circuit 40 may be essentially disposed inside the dialysis machine 300 but may also be structured differently, and comprises in detail components 42, 44, 54, 60 for processing the dialysate, the dialysate region 170 of the dialyzer apparatus 100, a dialyzer entry valve 72, and the dialysate inlet 74 for allowing the prepared dialysate to enter the dialysate region 170, a dialysate outlet 76, and a dialyzer exit valve 78 for allowing the used dialysate to exit the dialysate region 170 and for removing the dialysate to the elements 84, 80, and 86 of the dialysate exit. The components of the dialysate preparation typically comprise a water preparation unit 42 for providing a stream of prepared water into the dialysate supply lines 62, 62', a bicarbonate concentrate provided in a reservoir 44 that is dosed into the dialyzer supply line 62 in a metered amount via the bicarbonate inlet 48 with a controllable bicarbonate pump 46, an acid concentrate provided in a reservoir 54 that is dosed into the dialyzer supply line 62 in a metered amount via the acid inlet 58 with a metered acid pump 56, and an in-line balancing unit 60 located downstream of the inlets 48, 58 in the dialyzer supply line 62. The balancing unit 60 or a control unit contained therein or connected thereto is designed to control the composition and released amount, i.e., the dialysate flow, in a manner customized for the patient 10 and specific to the progression of the dialysis treatment, and in particular to generate the necessary control signals for the bicarbonate pump 46, the acid pump 56, a flow pump 64 disposed downstream of the balancing unit 60 in the dialysate supply line 62' for the dialysate supply, and a flow pump 84 disposed downstream of the dialysate region 170 in the dialysate outflow line 82, 82', and to control the flow pump 64 for the dialysate supply and the flow pump 84 for the dialysate outflow. The dialysate metered by the flow pump 64 and prepared upstream thereof flows through the dialyzer inlet valve 72 and the dialyzer inlet 74 into the dialysate region 170 of the dialyzer apparatus 100. After undergoing the material exchange with the blood of the patient 10 through the membrane of the membrane filter device 190, the dialysate flows on through the dialysate outlet 76 and is supplied to the dialysate outflow or removal system 84, 80, 86 via the dialyzer exit valve 78. The dialysate removal system comprises a balancing unit 80 typically disposed downstream of the dialysate outflow flow pump 84 in the dialysate outflow line 82, 82' and a dialysate removal 86 disposed downstream of the balancing unit 80 in the dialysate outflow line 82'. The dialysate removal 86 may be embodied, for example, as a collecting vessel that may be removed or disposed of. In many cases, however, the used dialysate may also flow directly into the drain and thus into a reprocessing segment or into the wastewater drainage system. The dialysate circuit 40 moreover comprises a bypass line 48 to the dialysate region 170 of the dialyzer apparatus 100. The bypass line 48 may be opened and closed with a bypass valve 66 and allows dialysate to bypass the dialysate region 170 and move from the dialysate inlet 64 directly to the dialysate outflow 84.

In detail, the extracorporeal blood circuit 20 comprises an arterial tube system 24, a blood region 130 of the dialyzer apparatus 100, and a venous tube system 34. During a hemodialysis treatment, the extracorporeal blood circuit 20 is installed by specialized medical personnel and comprises an arterial tube system 24 for conveying blood to be purified from the patient 10, the blood region 130 of the dialyzer apparatus 100, and a venous tube system 34 for conducting purified blood back to the patient 10. The arterial tube system 24 comprises an arterial access 22 to the arterial blood vessel system of the patient 10 that may be set up, for example, as an arterial needle or catheter, and an arterial blood pump 26 for pumping the arterial blood of the patient 10 from the arterial access 22, through the blood inlet 28, and into the blood region 130 of the dialyzer apparatus 100 and, further, through the venous tube system 34 to a venous access 36 in the venous blood vessel system of the patient 10. This arterial blood pump 26 may be connected via tube to or disposed on, for example, the arterial tube system 24. The venous tube system 34 conducts blood purified and/or treated in the dialysate region 130 from the blood outlet 32 of the dialysate region 130 back to the venous access 36 of the patient 10. This closes the extracorporeal blood circuit 20.

As already discussed above, in the schematic depiction of the dialysate circuit 40 and the blood circuit 20 shown in FIG. 1, the exchange of materials is occurring between the dialysate and the blood of the patient 10 in the dialyzer and/or in the dialyzer apparatus 100 according to the third aspect of the invention, more precisely, on the membrane of the membrane filter device 190 located therein. The latter component divides the internal volume portion 120 of the housing 110 of the dialyzer apparatus 100 into a dialysate region 170 through which the dialysate flows that is conveyed via the dialysate inlet 74 and removed via the dialysate outlet 76, and the blood region 130 through which the blood of the patient 10 to be treated and/or purified flows in through the blood inlet 28 and out through the blood outlet 32 and is conveyed back to the patient 10. The dialyzer apparatus 100 and/or the membrane filter device 190 disposed therein comprises a passive or active identification unit 192 that comprises an identification feature that is characteristic for the identification of the dialyzer apparatus 100 and/or the membrane filter device 190.

In one embodiment, the passive identification unit 192 is a passive RFID (radio frequency identification) chip, the identifying feature of which may be read by irradiating it with a predetermined electromagnetic radiation, the frequency of which lies, for example, in the RF (radio frequency) range. In another embodiment, the passive identification unit 192 comprises a code such as, for example, a barcode or a color code field, with the identifying feature being readable by irradiating it with electromagnetic radiation in the optical range having a wavelength in the infrared (IR), near infrared, visible, or ultraviolet (UV) light range.

A sensor device 200 according to the second aspect of the invention is operatively attached in a removable fashion to the dialyzer apparatus 100 according to the third aspect of the invention shown in FIG. 1. The sensor device 200 comprises a signal receiving unit 210 that is designed to receive at least one signal such as, for example, a radiation signal or an ultrasound signal, from the exterior or edge region or even from the internal volume portion 120 of the housing 110 of the dialyzer apparatus 100 and may also be attached externally on the housing or designed as a component of the housing. The received signal is characteristic of the state and/or the identification of the dialyzer apparatus 100 and/or the membrane filter 190 disposed therein. In one embodiment, the signal receiving device 210 comprises an identification reading unit 212 that is designed to detect a parameter of the radiation that is indicative of the identifying feature of the identification unit 192 and, in addition, to determine the identification of the dialyzer apparatus 100 and/or the membrane filter device 190. In order to allow the signal to reach from the internal volume portion 120 of the housing 110 to the signal receiving unit 210 disposed outside the housing 110, the housing 110 is essentially permeable to the signal at least in regions, or as a whole.

In order to irradiate the passive identification unit 192, the sensor device 200 comprises a radiation emitting unit 240 that is designed to emit the predetermined radiation, for example, electromagnetic radiation or ultrasound radiation, in order to contact the passive identification unit 192 so as to activate it to transmit modified electromagnetic or ultrasound-acoustic radiation containing the identifying feature and/or a parameter indicative thereof.

In the embodiment in which the passive identification unit 192 is a passive RFID chip, the radiation transmitting unit 240 comprises an RF radiation source (not shown). In the embodiment in which the passive identification unit 192 is a code such as, for example, a barcode, a data matrix, a general two-dimensional or three-dimensional code, for example, a colored 2-D code or a color code field, the radiation transmitting unit 240 comprises, for example, an optical or acoustical radiation source for contacting the code, and the identification unit 212 of the signal receiving unit 210 comprises, for example, a code scanner for reading the code such as a barcode scanner for reading the barcode or a camera, for example, with a two-dimensional CCD sensor or a 2-D code reader designed to detect the radiation, for example, optical light, reflected by the code, for example, the barcode or color code field, to analyze said radiation, and to recognize the indicative parameter and/or the identifying feature contained in the detected radiation.

In yet another embodiment, the dialyzer apparatus 100 or the membrane filter device 190 comprises an active identification unit 192 such as, for example, an active RFID chip, that is able to transmit electromagnetic radiation comprising an identifying feature that is characteristic for the identification of the dialyzer apparatus 100 or the membrane filter device 190. In this case, it is not necessary for a radiation transmitting unit for contacting the identification unit with a predetermined electromagnetic radiation to be provided in the sensor device 200. As is the case in the embodiments with a passive identification unit 192, the signal receiving unit 210 comprises an identification reading unit 212 that is designed to detect the electromagnetic radiation transmitted by the (in this case active) identification unit 192, for example, the active RFID chip, and, for example, after a demodulation analysis, recognize the identifying feature.

In yet another embodiment, the signal receiving unit 210 comprises a receiver for an electrical signal that is indicative of a capacity to be measured and/or an inductivity to be measured that is characteristic of the state and/or the identification of the dialyzer apparatus 100 and/or the membrane filter unit 190.

In yet another embodiment, the signal receiving unit 210 may be designed to receive signals from ultrasound radiation originating from the internal volume portion 120. The ultrasound radiation may be projected into the internal volume portion 120 and reflected in the dialysate region 170 and/or in the blood region 130 or may pass through these regions. In this embodiment, the signal transmitting unit 240 comprises an emitter for emitting ultrasound radiation into the internal volume portion 120, for example, focused in the dialysate region 170 or in the blood region 130 or in the region of the membrane of the membrane filter device 190. Ultrasound radiation influenced in the internal volume portion 120 by materials dissolved in fluid (dialysate or blood) located therein and/or by the membrane of the membrane filter device 190 may be arranged in a reflection arrangement, a transmission arrangement, or a scattering arrangement of the signal receiving unit 210 designed for the detection of ultrasound radiation relative to the signal transmitting unit 240 transmitting the ultrasound radiation.

In a reflection arrangement, the direction of the radiation to be detected—here, for example, ultrasound radiation—is directed essentially opposite, for example, at an angle of 180° or virtually 180°, the direction of the incoming radiation. The reflection may also occur at an angle other than 180° to the direction of the incoming radiation, i.e., for example, in an oblique direction or perpendicular direction. In a transmission arrangement, the direction of the radiation to be detected is directed essentially parallel, i.e., at an angle of 0° or virtually 0°, to the direction of the incoming radiation. In the case of a scattering arrangement, the direction of the radiation to be detected is directed at an angle essentially different from 0° or 180°, for example, 90°. The terminology used here for ultrasound radiation (reflection, transmission, and scattering arrangements) discussing radiation to be measured relative to the incoming radiation is used herein for optical electromagnetic radiation as well.

If the housing wall 110 is permeable at least in regions to optical electromagnetic radiation, i.e., in this instance to infrared (IR), near infrared, visible, or ultraviolet (UV) light radiation, then the sensor device 200 according to the second aspect of the invention may also be used to conduct optical measurements of various kinds directly on the dialyzer apparatus 100, from which information may be obtained regarding the state of the dialyzer apparatus 100 or the membrane filter device 190 or a property thereof, for example, a material concentration in the dialysate or blood or a value derived therefrom, or the speed in the fibers of the dialyzer apparatus, or the Brownian motion, or the dialysance of the dialyzer apparatus 100 or the membrane filter device 190. Optical measurements of this kind may be conducted in a reflection, transmission, and scattering arrangement, and moreover also in a refraction arrangement of a signal receiving unit 210 designed for the measurement of a light intensity with regard to an optical radiation transmitting unit 240. In one embodiment, the signal receiving unit 210 comprises an optical radiation measuring unit 220 and a second optical radiation detector 240 (see FIG. 2).

The sensor device 200 according to the second aspect of the invention may comprise a radiation transmitting unit 240 that is designed to transmit radiation, such as optical radiation (i.e., light) or ultrasound radiation into the internal volume portion 120 of the housing 110 of the dialyzer apparatus 100. Correspondingly, the signal receiving unit 210 may be designed to measure the intensity of electromagnetic radiation or ultrasound radiation exiting the internal volume portion 120 that was emitted by the radiation transmitting unit 240 into the internal volume portion 120. The radiation measured by the signal receiving unit 210 may be the result of an interaction of the emitted radiation characteristic of the state of the dialyzer apparatus 100 occurring in the internal volume portion 120 of the housing 110 between the radiation and one or more of the following substances: the dialysate in the dialysate region 170, the blood in the blood region 130, a material contained in the dialysate and/or in the blood, the membrane filter device 190, and a material held in or on the membrane filter device 190 that, for example, originated from the blood and/or the dialysate. Here, the interaction is triggered by the radiation transmitted by the radiation transmitting unit 214 into the internal volume portion 120 of the housing 110 and the portion of this radiation arrives after the interaction at the signal receiving unit 210 from the internal volume portion 120.

An optical interaction providing characteristic information for the state of the dialyzer apparatus 100 and/or the blood in the blood region 130 and/or the dialysate in the dialysate region 170 may be one of the following:

reflection of optical radiation (i.e., light) emitted by the radiation transmitting unit 240 onto a boundary surface between the wall 112 of the housing 110, for example, a window region 114, 116, 118 (see FIG. 2), and the dialysate or the blood, reflection of optical radiation emitted by the radiation transmitting unit 240 onto a boundary surface between the membrane filter device 190 and the dialysate or the blood, transmission of optical radiation emitted by the radiation transmitting unit 240 having a measurement wavelength, for example, in the infrared spectral range, that may be absorbed by a material contained in the dialysate and/or in the blood and that has passed along a beam path through the dialysate and/or through the blood on its way to the radiation receiving unit 220, emission of luminescent or fluorescent radiation by a material contained in the dialysate and/or in the blood, with the corresponding luminescent or fluorescent reaction having been provoked in said material by the optical radiation, for example, UV light, emitted by the radiation transmitting unit 240, refraction of optical radiation emitted by the radiation transmitting unit 240 onto a boundary surface between the wall 112 of the housing 110, for example, a window region 114, 116, 118 (see FIG. 2), and the dialysate or the blood, with the transmitting radiation striking, for example, at an angle of incidence between 0° and 180° or between 0° and 90°, scattering of optical radiation emitted by the radiation transmitting unit 240 onto a material contained in the dialysate or the blood, such scattering also including so-called dynamic scattering including, for example, Raman scattering of, for example, polychromatic or monochromatic light such as dichromatic, polychromatic, or monochromatic laser radiation; in such a case, an analysis may be conducted of the behavior of the scattered light over time for the purpose of analyzing a dynamic scattering; here, measurement is not limited to the analysis of the intensity—the phase of the electromagnetic radiation and its behavior over time can also contain information and be captured and analyzed instead of or in addition to the detection of the intensity, allowing the decay behavior of pulses over time to be analyzed as well;

interaction of optical radiation emitted by the radiation transmitting unit 240 with a passive identification unit 192 attached to the dialyzer apparatus 100 or the membrane filter device 190, such as a barcode field or a color code field, with the identification unit 192 having an identifying feature that is characteristic for the dialyzer apparatus 100 or the membrane filter device 190. Such applications have been described above.

Now referring to FIGS. 2A-C and 3A-C, the sensor device 200 according to the second aspect of the invention may be embodied as a clip arm or clip cuff 220 that may be attached directly to the housing 110 of the dialyzer apparatus 100 in a detachable and operatively connectable fashion, for example, may be clipped there. In the embodiment shown in FIGS. 2A-C and 3A-C, the sensor device 200 comprises two clip arms or clip cuffs 210, 210' that encompass the housing 110 which is, for example, cylindrical, and that are able to accommodate the housing therebetween.

In an embodiment as shown in FIGS. 2A-C, a clip arm or clip cuff 210 may have a shorter length relative to a length measured in a longitudinal direction 102 of the housing 110, and may correspondingly be shifted along the housing 110 in the longitudinal direction 102. In this embodiment, the sensor device 200 may be used to measure a desired parameter in a definable position along the longitudinal direction 102 of the housing 110 or may also be used to measure the variation of a parameter along the longitudinal direction 102 of the housing 110 with sequential measurements at various positions along the longitudinal direction 102.

In an alternative embodiment as shown in FIGS. 3A-C, a clip arm or a clip cuff 210 of the sensor device 200 may have a dimension relative to the longitudinal direction 102 of the housing 110 that is comparable along the length of the housing 110 and, correspondingly, may be designed to be only slightly slidable or not slidable at all along the longitudinal direction 102.

In general and also particularly in the embodiments shown in FIGS. 2A-C and 3A-C, it may be advantageous for the sensor device 200 to be able to be attached to the dialyzer apparatus 100 in one or more repeatable or reproducible, predetermined relative positions and/or orientations relative to said dialyzer apparatus. To this end, the housing 110 of the dialyzer apparatus 100 comprises on its exterior surface at least one coupling region 111 or, for example, two first coupling regions 111 and 111' disposed on the housing 110 essentially opposite one another disposed at predetermined positions on the apparatus 100. Correspondingly, the sensor device 200 comprises on its side facing the housing 110, for example, in FIGS. 2A-C and 3A-C, on an interior side of the clip arm or clip cuff 210, a second coupling region 211 or, for example, two coupling regions 211 and 211' that, when the sensor device 200 is connected to the apparatus 100, are essentially congruent to the coupling region or regions 111, 111' disposed on the housing 110. In the embodiment shown in FIGS. 2A-C, a plurality of first coupling regions 111 distributed in the longitudinal direction 102 of the housing 110, for example, at equal distances from one another, may be provided on the outer surface of the housing 110. These coupling regions allow the sensor device 200 to be attached in a removable fashion at various predetermined positions along the longitudinal direction 102 of the housing 110. The second coupling regions 211, 211' are designed to engage and cooperate with the first coupling regions 111, 111' such that the position of the sensor device 200 relative to the housing 110 of the apparatus 100 is well-defined and predetermined.

In one embodiment, the first coupling regions 111, 111' and the second coupling region 211, 211' comprise magnets that are attracted to one another. In another embodiment, the first coupling regions 111, 111' comprise so-called female receiving elements and the second coupling regions 211, 211' comprise so-called male plug elements that are designed to be received in the female receiving elements in a removable fashion. Preferably, these female receiving elements are assigned to the first coupling regions 111, 111' of the housing 110 of the dialyzer apparatus 100 and the male plug elements are assigned to the second coupling regions 211, 211' of the clip arms and/or clip cuffs 210, 210' of the sensor device.

In one, multiple, or all exemplary embodiments, the sensor device 200 and/or the dialyzer apparatus 100 may have a special shape, for example, one or more notches, recesses, or protrusions on or in the dialyzer housing that allow the clip, i.e., the sensor device, to be attached in a centered fashion only at that location.

Alternatively or additionally to the design described here of the sensor device 200 being connectable to the dialyzer apparatus 100 in a detachable and operative fashion, this may also be achieved by the following mechanically releasable mechanisms, in particular attachable with a positive fit:

The sensor device 200 is designed as a clip unit having at least one or even two (as shown in FIGS. 2A-C and 3A-C) or more flexible clip arms and/or clip cuffs 210, 210' that are designed to encompass the housing 110 of the dialyzer apparatus 100 in an angular range of more than 180°, preferably more than 270°, and even more preferably more than 320°.

The sensor device 200 comprises a base body (not shown) and a clip unit having at least one pair of elastically flexible clip arms and/or clip cuffs attached to the base body or clip arms and/or clip cuffs (not shown) articulated on the base body in an elastically flexible manner that are designed to accommodate the housing 110 or region of the housing 110 between one another. Due to their elastically flexible design or articulation, the clip arms and/or clip cuffs are able to encompass the housing 110 or part of the housing 110 in a clip-like fashion.

The sensor device 200 comprises a first member (not shown) of the connector unit (not shown) such as a dovetail unit, a screw, or a Velcro strip, and the dialyzer apparatus 100 comprises a second member and/or counter member (not shown) of this connector unit, such as a dovetail mount, a bore or screw thread, or an opposite piece to the Velcro strip. Here, the first member is able to engage in the second member or the second member is able to engage in the first member in a removable, positive fitting fashion.

The sensor device 200 is clamped to the housing 110 with an elastic clamping unit (not shown), such as a rubber ring. Here, the clamping unit may be designed to encompass the sensor device 200 and the housing 110 of the dialyzer apparatus in its elastically tense state.

The sensor device 200 comprises at least one pair of arms and/or cuffs, each of which comprises a distal end region with a first member of a hook or engaging unit. Here, the arms and/or cuffs are designed to encompass the housing 110 in an angular range of more than 180°, preferably more than 270°, and more preferably more than 320°. Moreover, an elastically tensible clamping unit having two opposite end sections is provided, on each of which a second member or counter member of the hook or engaging unit is provided for detachably engaging a first member of the hook or engaging unit. Here, in an elastically tense state of the clamping unit, a respective second member on the end section of the clamping unit can engage with a first member on the end regions of the arms and/or cuffs of the sensor device 200, such that the arms and/or cuffs of the sensor device 200, along with the elastically tense clamping unit, completely surround or encompass the housing 110. Optionally, the sensor device 200 may comprise a base body (not shown) on which the arms and/or clamps are articulated or to which the arms and/or clamps are connected in an elastically flexible fashion.

The sensor device 200 is designed to be integrated in a detachable fashion, for example, into a recess in or on the wall 112 of the housing 110 of the dialyzer apparatus 100. This embodiment is particularly suitable when the sensor device 200 has a spatially small expansion, such as in the case of an RF identification reading unit 212.

In the embodiment of a system according to the first aspect of the invention shown in FIGS. 2A-C having a sensor device 200 according to the second aspect of the invention, the housing 110 of the dialyzer apparatus according to the third aspect of the invention is not sufficiently permeable or transparent for optical radiation (i.e., light). Therefore, so-called window regions 114, 116, 118 are provided in the wall 112 of the housing 110 that are sufficiently permeable or transparent for optical radiation. The radiation transmitting unit 240 is integrated into the clip cuffs 210 that comprises a first, for example, optical, or other kind of radiation source 242 for emitting electromagnetic radiation, for example, light, into the blood region 130 and a second, for example, optical, radiation source 244 for emitting electromagnetic radiation, for example, light, into the dialysate region 170. Moreover, a radiation measuring unit 220 is integrated into the clip arm or clip cuffs 210, 210' having a first, for example, optical, radiation detector designed to detect electromagnetic radiation, for example light, exiting the blood region 130 and a second, for example, optical, radiation detector that is designed and suitably arranged for detecting electromagnetic radiation, for example, light, exiting the dialysate region 170. Here, the first radiation detector 222 is designed to measure electromagnetic radiation, for example, light, exiting the blood region 130 that was projected in that direction by the first radiation source 242. The second radiation detector 224 is designed to detect the electromagnetic radiation, for example light, exiting the dialysate region 170 that was projected in that direction by the second radiation source 244.

In one embodiment, the first radiation detector 222 is spatially disposed or positioned relative to the first radiation source 242 and the blood region 130 in such a way that the light emitted by the first radiation source 242 into the blood region 130 by the second radiation detector 224 in a reflection arrangement in which only reflected or backward dispersed light is measured. In another embodiment, the first radiation detector 222 is disposed relative to the first radiation source 242 and the blood region 130 in a transmission arrangement in which essentially only light is measured that has undergone scattering in an essentially forward direction or transmission in the direction of a well-defined path through the blood region 130. In yet another embodiment, a scattering arrangement is realized in which a field of view of the first radiation detector 222 is measured relative to a primary emitting direction of the first radiation source 242 at an angle, preferably an angle of approximately 90°, but in any event at an angle that substantially differs from 0° and 180°. The same statements apply for the second optical radiation detector 224 and its arrangement or position relative to the second radiation source 244 and the dialysate region 170.

In the embodiment of a system according to the first aspect of the invention shown in FIGS. 3A-C, the sensor device 200 according to the first aspect of the invention is designed in such a way that it almost completely encompasses and covers the housing 110, which is cylindrical in the example, of the dialyzer apparatus 100 according to the third aspect of the invention. This is realized in the example of FIGS. 3A-C by the design of the sensor device 200 in the form of a clip cuff 210, 210'.

FIG. 3C, the interior of the sensor device 200 is shown that has been opened, removed from the housing, and unrolled to be flat; this interior faces the dialyzer apparatus 100 when the sensor device is attached to it. In the essentially rectangular inner surface of the sensor device 200, a plurality of radiation entrance regions 230, 232-x, 232-y, 236-x,y and a plurality of radiation exit regions 250, 252-x, 254-y, 256-x,y are formed. For purposes of designating and defining directions, the direction of the longitudinal axis 102 and the direction of the circumference 104 of the housing 110 of the dialyzer apparatus 100 for the unrolled sensor device 200 have been drawn into FIG. 3C with dashed lines.

In one embodiment, the plurality of radiation entrance regions 230 forms a one-dimensional arrangement 231 of radiation entrance regions 232-x, for example, oriented in the direction of the circumference 104, that may extend over part of the circumference or, in one or more exemplary embodiments, also essentially over the entire extension along the circumferential direction 104 of the sensor device 200. In an embodiment that may be realized additionally or as an alternative, a plurality of the radiation entrance regions 230 forms a second one-dimensional arrangement having a plurality of radiation entrance regions 234-y that may extend over a part of or, in one or more exemplary embodiments, essentially over the entire extension of the sensor device 200 along the direction of the longitudinal axis 102. In an additional embodiment, the radiation entrance regions 230 form a two-dimensional arrangement 235 having a plurality of radiation entrance regions 236-x,y that may be disposed in a regular arrangement orientated in a direction oblique or parallel to the direction of the circumference 104 and the direction of the longitudinal axis 102, for example, a rectangular lattice arrangement, or may also be disposed in an irregular form. Here, this two-dimensional arrangement 235 or lattice arrangement extends over a part of or, in one or more exemplary embodiments, also essentially over the entire surface of the sensor device 200. The arrangement of the radiation entrance regions need not extend over the entire sensor device, but rather may also be present only in partial regions that are of particular interest.

Arranged in each radiation entrance region 230, 232-x, 232-y, 236-x,y, is either a radiation receiver, in particular a light detector, or the entrance of an optical light guide or a light-conducting fiber. In the latter case, the optical light guide or the light-conducting fiber conducts the light that has entered into the optical light guide or light-conducting fiber through the optical light guide or light-conducting fiber to a radiation exit region on the opposite end of the optical light guide or light-conducting fiber, where a light detector is provided that detects light exiting the optical light guide or light-conducting fiber. Depending on the measurement task and light intensity or wavelength to be expected, each light detector may be one of the following: a photodiode, a phototransistor, a CMOS light detector, a photomultiplier, or an avalanche photodiode. In the embodiment with optical light guides or light-conducting fibers, the light exit ends may be combined to form a lattice arrangement congruent to the arrangement of the light entrance openings and the light exiting from the plurality of these exit openings may be measured on a correspondingly arranged or equipped one-or two-dimensional light detector, for example, a one-or two-dimensional CCD sensor, in its spatial distribution and with regard to its intensity.

Corresponding to the spatial arrangement of the radiation entrance regions 230 in one-dimensional arrangements 231, 233 or in a two-dimensional arrangement 235, the plurality of radiation exit regions 250 may be designed in one of the following arrangements: a one-dimensional arrangement 251 of radiation exit regions 252-x that are distributed along the direction of the circumference 104 and that extend essentially over the entire extension of the unrolled sensor device 200, a one-dimensional arrangement 253 of radiation exit regions 254-y that are distributed along the direction of the longitudinal axis 102 and that essentially extend over the entire extension in this direction of the unrolled a sensor device 200, and/or a two-dimensional arrangement 255 of a plurality of radiation exit regions 256-x,y that are disposed in an essentially rectangular lattice arrangement oriented along the direction of the circumference 104 and the longitudinal axis 102. Either a light source such as an LED or an exit opening for the exit of light from an optical light guide or light-conducting fiber conducting light may be disposed in each radiation exit region 250. In the embodiment with optical light guides or light-conducting fibers conducting light, a separate light source may be disposed on the opposite end of each optical light guide or light-conducting fiber. Alternatively, the radiation exit regions 250 may also be combined in a lattice arrangement, for example, congruent to the lattice structure of the radiation entrance regions 230 and may be illuminated by a plurality of radiation sources or even by one single light source that, for example, emits a homogenous radiation field or parallel light, such as an expanded laser beam. Other light sources may be used as well, for example, such as one or more halogen lamps or other lamps, fluorescent light sources, or the like. If multiple light sources are used, the light sources may be switched on and off individually in one, multiple, or all exemplary embodiments, such that a targeted and controlled irradiation may be conducted.

As a person skilled in the art will easily see, different light irradiation distributions and/or illumination geometries may be realized by the selective activation or radiation emission from the radiation exit regions 250. By the selective measurement of radiation intensities in selectively chosen radiation entry regions 230, various radiation or illumination configurations of light from the housing 110 of the dialyzer apparatus 100 may be realized.

In the embodiment in which radiation is conducted from the radiation entry regions via an optical light guide and/or a light-conducting fiber to a detector located at a spatial distance, a light measuring unit may also be provided behind the light exit region from the optical light guide and/or light-conducting fiber that may comprise a wavelength selection unit such as a monochromator and a light detector disposed therebehind. The wavelength selection unit may be designed to select a narrow wavelength range that includes a predetermined detection or measurement wavelength.

For example, a narrow-band wavelength range of measurement wavelengths may be realized or scanned in such a way that a luminescent or fluorescent emission spectrum may be detected. A person skilled in the art knows that a luminescent, fluorescent, or fluorescence emission spectrum is characteristic for a selected material that is dissolved, for example, in the blood region 130 or in the blood, or in the dialysate region 170 or in the dialysate. Here, in one or more exemplary embodiments, such a luminescent or fluorescent material may be applied to the housing that is able to identify the dialyzer. Thus, the type of dialyzer may be recognized that is currently inserted, currently being used, or to be used.

Figure 4:
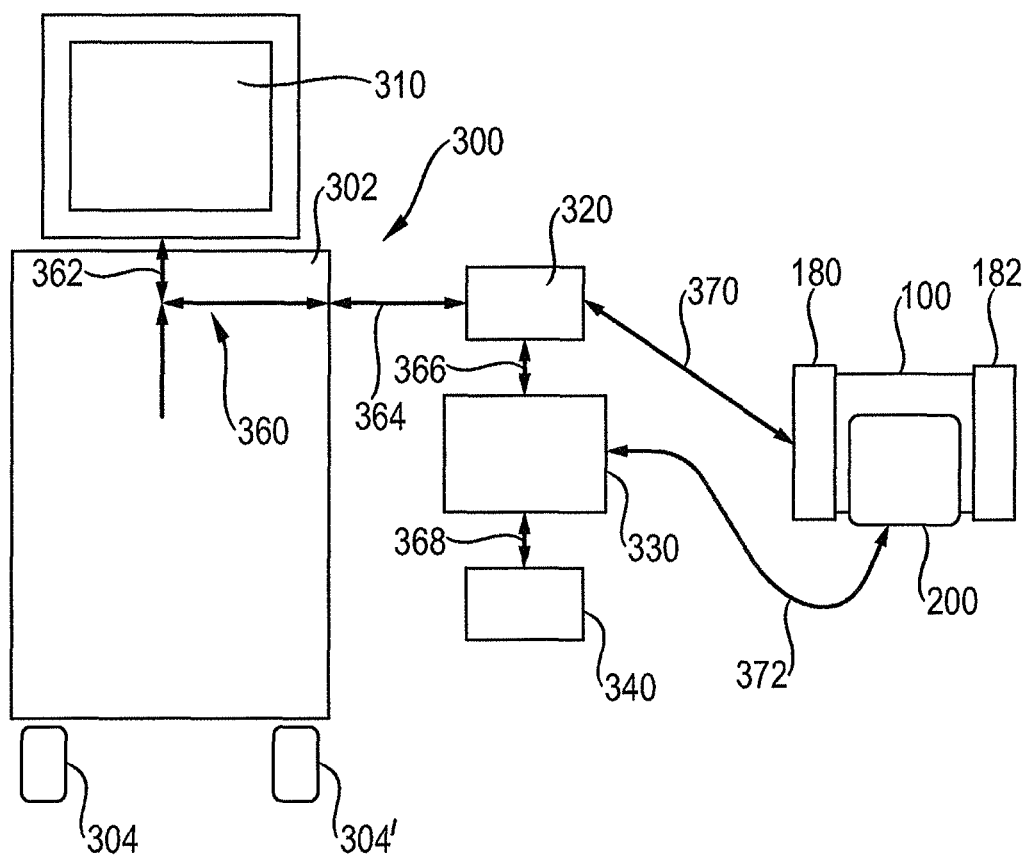
FIG. 4 a block diagram of a dialysis machine and its functional components, including an embodiment of a system having an embodiment of the sensor device that is detachably connected to an embodiment of a dialyzer apparatus.

FIG. 4 shows how a dialyzer apparatus 100 according to the third aspect of the invention and a sensor device 200 according to the second aspect of the invention may be integrated into or connected to a dialysis machine 300 according to the fourth aspect of the invention with regard to control and/or reading and conducting of measurement and control signals. The dialysis machine 300 shown in FIG. 4 comprises the components of the dialysate circuit 40 and the blood circuit shown in FIG. 1, which are not shown in detail in FIG. 4.

The dialyzer apparatus 100 is fluidically integrated into the dialysate circuit 40 of the dialysis machine 300 via the dialysate supply 72 and the dialysate discharge 78 shown in FIG. 1. Moreover, the dialyzer apparatus 100 is connected to the arterial access 22 and the venous access 36 of the patient 10 via the arterial tube system 24 and the venous tube system 34, see FIG. 1.

The dialysis machine 300 shown in FIG. 4 comprises a machine housing 302 in which the components of the dialysate circuit 40 shown in FIG. 1 are disposed, with the exception of the dialyzer apparatus 100. The dialyzer apparatus may be disposed inside the machine housing 302 or externally thereto. In the case of an external arrangement, the dialyzer apparatus 100 is in fluidic communication with the components of the dialysate circuit 40 disposed inside the machine housing 302 via the dialysate supply 72 and the dialysate outlet 78, see FIG. 1. The machine housing 302 comprises housing rollers 304, 304' with which the machine 300 may be rolled along a floor. A data output and/or visualization unit 310 and a data input unit (not shown) are provided disposed on the machine housing 302 or at a distance therefrom and connected via the corresponding data lines. The data input unit and data output and/or a visualization unit 310 combine to form an input/output unit that may be structured in any manner corresponding to the wide variety of modern human-machine interfaces known to the person skilled in the art.

The dialysis machine 300 also comprises a control unit 320 that is designed to control the components of the dialysate circuit 40, the radiation transmitting unit 210 and its components, as well as to control the radiation measuring unit 240 and its subcomponents, a data processing and/or analysis unit 330 that is designed to receive the measurement signals generated by the sensor device 200, to convert said signals into relevant parameters, analyze them, and provide them for storage and/or backup, and a storage unit 340 that is designed to receive and store measurement data provided and/or analyzed by the data processing and/or analysis unit 330, and in particular also computer programs that control the controlled unit 320, the data processing and/or analysis unit 330 and/or the input/output unit 210.

The dialysis machine 300 moreover comprises a data bus system 360 at which the control components of the dialysate circuit 40 and the blood circuit 20, the units 310, 320, 330, 340 shown in FIG. 4, and the dialyzer apparatus 100 and the sensor device removably attachable thereto are communicatively connected to one another. The data bus system 360 comprises an input/output data line 362 with which the input/output unit 310 is communicatively connected, a control line 364 with which the control unit 320 is communicatively connected and made able to receive data from the input/output unit 310 and the transmit control data and/or analyze data to the input/output unit 310, for example, to be output as a display, an operating data line 366 with which the control unit 360 and the data processing and/or analysis unit 330 are communicatively connected to one another, a data storage line 368 with which the storage unit 340 and the data processing and/or analysis unit 330 are communicatively connected to one another, the dialyzer apparatus signal line 370 with which the dialyzer apparatus 100 and the dialysis machine 300 are communicatively connected to one another, and a sensor device signal line 372 with which the sensor device 200 and the data processing and/or analysis unit 330 of the dialysis machine 300 are communicatively connected to one another.

The dialyzer apparatus 100 is connected to the control unit 320 via the dialyzer apparatus signal line 370 and the sensor device 200, which is removably attachable to the dialyzer apparatus 100, is communicatively connected to the data processing and/or analysis unit 330 of the dialysis machine 300 via the sensor device signal line 372. Via the sensor device signal line 372, the data processing and/or analysis unit 330 is able to transmit measurement data, for example, measured radiation intensity data or identification data, generated by the sensor device 200 to the data processing and/or analysis unit 330 for processing and analysis as well as receive control data for controlling the radiation transmitting unit or units 240 from the control unit 320. Via the dialyzer apparatus signal line 370, the dialyzer apparatus 100 is able to receive control signals from the control unit 320 and, conversely, transmit information that is characteristic for its state and/or identification to the control unit 320.

The dialysis machine 300 shown in FIG. 4 moreover comprises a first housing holder 180 and the second housing holder 182. These housing holders are designed to carry the dialyzer apparatus 100 between them in a removably insertable fashion. The first housing holder 180 and, optionally, the second housing holder 182 may be designed as end caps to be removably placed on the respective end of the dialyzer apparatus 100 and, in particular, to be reusable, while the dialyzer apparatus 100 as a whole is designed as a single-use article. Here, the housing holders 180, 182 serve to fluidically integrate the dialyzer apparatus 100 into the dialysate circuit 40 and the blood circuit 20. The sensor device 200 may be permanently connected to the first or second housing holder 180, 182 or maybe designed separately therefrom.

In one embodiment, the first housing holder 180 is connected in a fixed fashion to the housing 110 of the dialysis machine 300 and the second housing holder 182 is designed as a separate part that is removably attachable, for example, clipable, to the dialyzer apparatus 100 and also removably attachable, for example, clipable, to the machine housing 302. In another embodiment, only one single housing holder 180 is provided that holds the dialyzer apparatus 100 in a removable, for example, clipable, and reliable fashion. In yet another embodiment, the dialyzer apparatus 100 and the housing holders 180 and 182 are used at a remove from the dialysis machine, for example, near the patient 10 to be treated.

It is obvious to the person skilled in the art that the sensor device 200, in particular in the embodiments described in FIGS. 2A-C and 3A-C, as a whole may be designed in such a way that the following functions and/or concretely structured optical measurements may be conducted at the dialyzer apparatus 100. The functionality of the sensor device 200 shown in FIGS. 3A-C may, for example, be completely adapted for the following tasks:

(i) measurements in the blood region 130 for determining the concentration of materials such as, for example, albumin, other materials, or uremic toxins, in the blood,
(ii) measurement of physical parameters of the blood in the blood region 130 and/or the dialysate in the dialysate region 170, for example, viscosity and/or flow rate of the dialysate and/or the blood or the hematocrit concentration in the blood, and
(iii) measurements in the dialysate region 170 to determine the concentration of materials such as, for example, proteins, other materials, or uremic toxins in the dialysate.

Exemplary embodiments of optical measurements that may be conducted using the sensor device 200 will be described in the following.

1. Measurements on the Dialyzer Apparatus

A light source is provided that is built into the sensor device 200 described with reference to FIGS. 2A-C or optically connected thereto via optical light guides and/or light-conducting fibers; said light source emits narrow-band light, for example, an LED, a laser beam, or a monochromatic light-guiding optical light guide and/or light-conducting fiber. This light source shines light, optionally via a beam-forming element, for example, a collecting lens, vertically or at a predetermined angle through a transparent area, for example, a window region 114, 116, 118, into the internal volume portion 120 of the housing 110. The projected light impacts in the region of the dialyzer apparatus 100 in which the membrane of the membrane filter device 190 is disposed with its membrane fibers. A light detector is integrated in the spatial vicinity of the light source into the sensor device 200 or optically connected thereto via an optical light guide and/or light-conducting fiber, said light detector capturing light scattered or reflected into its field of view that is reflected, for example, on the housing, on the boundary surface between the housing and the fluid, or in the region of the internal volume portion 120 illuminated by the light source. This light detector may be one photodiode or a plurality of photodiodes or also another type of detector such as a phototransistor, a CMOS detector, a CCD, a photomultiplier, or an avalanche photodiode.

A one-dimensional arrangement 231, 233 or a two-dimensional arrangement 235 of light detectors and/or light entry openings (radiation entry regions 230) is distributed over the interior side of the sensor device 200 having the input ends of optical light guides and/or light-conducting fibers, whose light input bevels point in the direction of view from which the light radiation to be analyzed comes. The optical light guide and/or light-conducting fibers serve to conduct the light to be analyzed out of the sensor device 200 to another place to be analyzed, for example, with the light detectors mentioned above, optionally in combination with wavelength selection units (for example, monochromator(s)). The selection of measurement wavelengths allows the selection of materials dissolved in the dialysate and/or in the blood with which the analyzed light has interacted. The entry and/or exit of the light may also occur at an angle to the surface of the housing; in such a case, the light detectors or optical light guides may be disposed obliquely to the surface of the housing.

For example, in the green spectral range (500-600 nm), the light primarily interacts with the hemoglobin in the blood. Hemoglobin has absorption bands in this spectral range. In the infrared spectral range, glucose (for example, at the wavelength 2.3 µm) and urea (for example, at a wave number (reciprocal wavelength)) contained in the blood absorb in the range of approximately 4500 to 4700 $cm^{-1}$.

In the radiation inlet regions 230 of the sensor device 200, it is also possible for one or more radiation measuring units 220 to be disposed having a measurement optic unit with a focus and/or focal direction and a light detector having a light-sensitive detector surface. Here, the measurement optic unit may be designed to map a spatial region from the internal volume portion 120, for example, from the blood region 130 or the dialysate region 170 onto the detector surface of the light detector, with the spatial region to be mapped being defined by adjusting the focal depth and focal direction. By changing the focal depth and optionally also by changing the focal depth of the detected light, the area of the internal volume portion 120 in which an optical interaction occurs may be selected. A specific analyte to be detected may be selected by selecting the measuring wavelength.

In the interactions of reflection, absorption, and transmission, the wavelength of the analyzed light is equal to the wavelength of the projected light beam. In one or more exemplary embodiments, the light beam may be projected essentially vertically onto the housing wall 112 of the dialyzer apparatus 100 and analyzed in the same direction or even at a right angle (or a virtual right angle) thereto, for example, if fluorescence properties are used. In this measuring arrangement, a low intensity of analyzed light may indicate the presence of a high degree of absorption, which in turn allows conclusions to be drawn on the concentration of a material or mixture of materials, for example, causing absorption. Thus, a change over time and spatial distribution of the absorption may be detected and thus a spatial distribution and/or a change over time in a material concentration may be measured.

2. Fluorescence and/or Luminescence Measurements on the Dialyzer Apparatus

If the wavelength of the analyzed light beam is a different wavelength, for example longer wavelength, then that of the projected light beam, the measuring arrangement described above may be used with a scattering arrangement of the direction of view of the light detector relative to the projection direction of the light source at a corresponding intensity and selection of the wavelength of the projected light beam, for example, in the ultraviolet (UV) spectral range, to measure and optionally also quantify fluorescent and/or luminescent interactions induced with materials dissolved in the blood or in the dialysate. Here it is possible in one or more exemplary embodiments for the light beam inducing the interaction to be projected in brief and, for example, high-intensity, pulses of light and to detect the light generated and/or spectrally dispersed as a result of the fluorescent and/or luminescent reaction. Such fluorescence and/or luminescence measurements allow conclusions to be drawn regarding materials dissolved in the dialysate and/or in the blood as well as their concentration and spatial distribution. This allows a time-resolved measurement in which the decay time of the fluorescence is measured as a characteristic.

Instead of pulses, a continuous illumination may also be provided.

In one or more exemplary embodiments, the detector is disposed at an angle, for example, at a right angle to the light incidence direction, such that the measurements are disturbed by reflections either negligibly or not at all.

3. Refraction of Light Radiation at the Dialyzer Apparatus

The possible structures of light irradiation and light detection from example 1 apply here correspondingly. Concretely, they may be used to measure light refraction at the dialyzer apparatus 100 as follows:

Irradiated light radiation is projected in a well-defined direction onto the housing wall 112, not vertically but rather at any desired oblique angle on the housing wall 112. Light refraction occurs at the boundary surface between the housing wall 112 and the dialysate or the blood as well as at all other boundary surfaces in the internal volume portion 120 of the dialyzer apparatus 100. As is known to the person skilled in the art, these refractions depend on the refraction index of the materials present at the boundary surfaces. Due to their concentration and their strong optical interactions, the optical properties of the dialysate and the blood have the greatest effect on light refraction. The measurement of light refraction may therefore be referred to for the analysis of physical properties of the dialysate and/or the blood, for example, to measure their density.

The detection of refracted light radiation exiting the dialyzer apparatus 100 after refraction may occur in a space-resolved fashion at a site of the sensor device 200 different from the irradiation site. The location of the detection, for example, by selectively choosing active light entrance openings 256-$x,y$ in the two-dimensional arrangement 255 in FIGS. 3A-C, and the irradiation direction and location of the irradiated light may be coordinated with one another such that the angle of refraction undergone in the course of the light refraction from the position of the detected refracted light within the two-dimensional arrangement 255 of the radiation entrance openings 256-$x,y$ may be inferred. From this, the complex refraction index may be inferred and, in turn, the physical properties of the liquids in the dialysate and/or in the blood influencing the refraction index, for example, their density, may be inferred. Medically relevant parameters may be derived from the physical properties, such as the hematocrit concentration in the blood.

4. Transmission Measurements on the Dialyzer Apparatus

If the view direction of a detector in the sensor device 200 is placed at one site and oriented on the irradiated incident light beam, it is possible to determine an absorption coefficient along the path traveled by the light beam from the dampening and/or from the removal from the light beam upon traveling a path in the internal volume portion 120, for example, in the blood region 130 or in the dialysate region 170. If the light beam is selectively measured with regard to the absorption wavelength, the selection of the measurement wavelength allows a material-specific absorption to be measured and a concentration of the corresponding material in the space along the path traveled by the light to be inferred. Such transmission and absorption measurements allow conclusions to be drawn regarding the material composition of the dialysate and/or the blood.

5. Measurement of Scattered Radiation at the Dialyzer Apparatus

With the measurement geometry described in examples 1 and 2, light radiation scattered in the dialyzer apparatus 100 may also be analyzed. To this end, the intensity of the scattered light may be determined at any desired position on the dialyzer apparatus that, if possible, is not located in the direction of propagation of the scattered light or in the direction of propagation of the reflected light. Preferably, the scattered light is measured at multiple locations on the housing surface 112 of the dialyzer apparatus, which is possible, for example, using the embodiment shown in FIGS. 3A-C of the sensor device 200 having a two-dimensional arrangement 255 of light entrance openings 256-$x,y$.

From the intensity of the scattered light, the presence of materials may be inferred, for example, certain molecules whose dimensions are typically up to 10 times smaller than the wavelength of the light used. The larger the concentration of such materials and/or structures, the greater the intensity of the scattered radiation. From the spatial distribution of the intensity of the scattered radiation in the different spatial directions, the size and the shape of the materials and/or structures (for example, molecules) may be inferred.

A special case of light scattering inducible using the sensor device 200 is dynamic light refraction. Here, a highly monochromatic and highly directed and/or concentrated light source such as a laser beam is used as a light irradiation unit 210. Using the two-dimensional light detection arrangement, such as the two-dimensional arrangement 255 of the light entrance openings 256-$x,y$ in FIGS. 3A-C, the spatial distribution of the scattered light may be measured. The spatial distribution is influenced, inter alia, by interference of the scattered irradiated light, with light reaching the same point of the two-dimensional (planar) detector unit from the one irradiated light beam via different paths (scattering paths). From the measured change over time of the interference pattern measured with the planar detector unit, the movement of the scattering centers may be inferred. If the analyzed scattering centers are, for example, red blood cells, their speed may be inferred, in particular the speed of their (undirected) Brownian motion, and from that their tendency to coagulate the blood in capillaries of the membrane of the membrane filter device 190 and, based on that, changes may optionally be made in the parameters of the dialysis therapy.

6. Electromagnetic Identification of a Dialyzer and/or the Membrane Filter Device used in Dialysis Therapy Electromagnetic radiation may also be used to identify the dialyzer apparatus 100 and/or membrane filter unit 190 used in a dialysis therapy on a patient 10 in an automated fashion. Thus, the dialysis machine 300 may obtain information regarding the dialyzer apparatus or membrane filter device 190 designed as a single-use article (held, for example, by the housing holders 180, 182) used in the dialysis therapy of a patient 10, for example, the type and/or a serial number or some other special embodiment thereof without medical personnel conducting the therapy being required to enter information regarding the identification of the dialyzer apparatus 100 and/or membrane filter device 190 used in the dialysis therapy in a potentially erroneous fashion, for example, via the input/output unit 310 of the dialysis machine 300.

In one embodiment, a barcode scanner, a detector, or a camera (for recognizing a code, for example, a data matrix and/or a 2-D code or a fluorescent code) is integrated into the sensor device 200 for this purpose, and the sensor device 200 is placed on the dialyzer apparatus 100 in such a way that the barcode scanner and/or the detector or the camera is able to read a code attached or printed on the dialyzer apparatus 100 or membrane filter device 190 embodied as a single-use article, for example, a barcode and/or data matrix and/or 2-D or 3-D code or a fluorescent code. Using optical detectors, a color code identification may also be realized, such as a color code attached to or printed on the single-use article or via a colorful design of the dialyzer housing 110 or via a spectrometric and/or a true-color light detector unit, thus realizing an identification of the dialyzer apparatus 100 or membrane filter device 190 used in the dialysis therapy.

As an alternative to identification based on optical detection by the sensor device 200, a communication may be initiated based on the measurement of RF (radio frequency) radiation with an RFID chip attached on the dialyzer apparatus 100 or on the components such as the membrane filter device 190 and stored on the RFID chip in a manner known to the person skilled in the art and characteristic identifying information may be accessed. One advantage of identification with RF radiation is the fact that the RF detector integrated into the sensor device 200 may be designed with a very short range, for example, inductively, thus ensuring with a high degree of certainty that only the RFID chip attached to the dialyzer apparatus 100 currently attached to the sensor device 200 will be read.

The embodiments of the sensor device 200 according to the second aspect of the invention described herein and/or claimed in the attached claims and of the dialyzer apparatus 100 according to the third aspect of the invention allow the following advantages to be attained in a manner obvious to the person skilled in the art:
1) Measurements of information regarding a state, for example, a dialysance, or a material concentration, or regarding an identification of a dialyzer apparatus 100 or membrane filter device 190 designed as a single-use article during operation in a dialysis treatment of a patient 10.
2) Measurements with a comparably high temporal resolution, for example, in time intervals of a few seconds to minutes, that allow therapeutic interventions for the optimization of treatment to be undertaken during an ongoing dialysis treatment.
3) Measurements, in particular conducted in a contact-free fashion, of information regarding the state of the dialyzer apparatus 100 or the membrane filte device 190 directly on the dialyzer apparatus 100.
4) The sensor device 200 is reusable and therefore cost-efficient in light of the fact that the dialyzer apparatus 100 or at least the membrane filter device 190 disposed therein is a single-use article. This advantage will continue to be valid until some point in the future when sensor equipment to be integrated into the dialyzer apparatus 100 becomes less expensive.

The invention claimed is:

1. A system for detecting a property or a state of a dialyzer apparatus or a component thereof before or during the operation of the dialyzer apparatus or before or during a blood treatment, the system comprising:
the dialyzer apparatus having a housing encompassing an internal volume portion and a membrane filter device disposed in the internal volume portion, the housing permeable at least in regions to radiation; and
a sensor device that is adapted to be connected directly to the housing of the dialyzer apparatus in a detachable fashion and that comprises a signal receiving unit configured to receive at least one radiation signal from at least the internal volume portion of the housing, with the at least one radiation signal being characteristic of the dialyzer apparatus, the state of the dialyzer apparatus, or the blood treatment.

2. The system according to claim 1, the system configured to provide a control signal of an analysis unit that generates data on the basis of the received at least one radiation signal that may be used for controlling the operating parameters of a dialysis machine.

3. The system according to claim 1, wherein the signal receiving unit is designed to receive or detect radiation selected from a group that comprises the following:
a) electromagnetic radiation of the entire electromagnetic spectrum;
b) electromagnetic radiation of the entire electromagnetic spectrum with a wavelength in the optical range;
c) electromagnetic radiation having a wavelength or a frequency corresponding thereto in the microwave range, in the terahertz range, or in the range of radio waves; and
d) ultrasound radiation.

4. The system according to claim 1, wherein the signal receiving unit comprises a receiver for an electrical signal, with the electrical signal being indicative of at least one of a capacity to be measured or an inductivity to be measured that is characteristic of at least one of the state of the dialyzer apparatus, or an identification of the membrane filter device.

5. The system according to claim 3, wherein the sensor device further comprises a radiation transmitting unit configured to transmit a desired radiation into the internal volume portion of the housing of the dialyzer apparatus;
wherein the signal receiving unit is configured to measure one or more parameters of the intensity, phase, or the behavior over time of radiation emitted by the radiation transmitting unit; and wherein the measured radiation is the result of an interaction characteristic for the state of the dialyzer apparatus that has occurred in the internal volume portion of the housing between the radiation and at least one of:
dialysate,
blood,
a material contained in the dialysate,
a material contained in the blood,
the membrane filter device, or
a material held in and/or on the membrane filter device originating from the blood and/or the dialysate,
with at least a portion of the measured radiation having arrived from the internal volume portion to the signal receiving unit, and
with the interaction characteristic being incurred by the emitted radiation from the radiation transmitting unit into the internal volume portion of the housing.

6. The system according to claim 5, wherein an optical interaction is incurred that has been selected from a group that comprises the following:
reflection of optical radiation emitted by the radiation transmitting unit on a boundary surface between a wall of the housing and the dialysate or the blood,
reflection of optical radiation emitted by the radiation transmitting unit on a boundary surface between the membrane filter device and the dialysate or the blood,
transmission of optical radiation emitted by the radiation transmitting unit having a measuring wavelength that can be absorbed by a substance contained in the dialysate and/or in the blood and, on its way to the radiation receiving unit, has followed a beam path through the dialysate and/or through the blood,
emission of luminescent or fluorescent radiation by a material contained in the dialysate and/or in the blood, with a luminescent or fluorescent reaction in said material being triggered by the optical radiation emitted by the radiation transmitting unit, refraction of the optical radiation emitted by the radiation transmitting unit to a boundary surface between the housing wall and the dialysate or the blood, with the transmitted radiation striking the boundary surface at an angle of incidence between 0° and 180°, refraction of the optical radiation emitted by the radiation transmitting unit to a boundary surface between the housing wall and the dialysate or the blood, with the transmitted radiation striking the boundary surface at an angle of incidence between 0° and 90°, scattering of optical radiation emitted by the radiation transmitting unit on a substance contained in the dialysate or in the blood, including dynamic scattering of monochromatic laser radiation, and interaction of optical radiation emitted by the radiation transmitting unit with an identification unit attached to the dialyzer apparatus or the membrane filter device that comprises an identifying feature characteristic for the identification of the dialyzer apparatus or the membrane filter device.

7. The system according to claim 5, in which the radiation transmitting unit comprises at least one of:

a light source that transmits light in a narrow-band spectral range, a light-conducting fiber that guides light transmitted by a light source emitting light in a narrow-band spectral range and a decoupling segment from which the light exits, a light source that transmits light in a wide-band spectral range, or a light-conducting fiber that guides light transmitted by a light source emitting light in a wide-band spectral range and a decoupling segment from which the light exits.

8. The system according to claim 7, in which the radiation transmitting unit comprises a one-dimensional arrangement or a two-dimensional arrangement of a plurality of light exit regions, in which the arrangement in the connected state of the sensor device and the dialyzer apparatus is oriented transversely, obliquely, or parallel to a flow direction of the dialysate in a dialysate region or transversely or obliquely or parallel to the flow direction of the blood in a blood region or transversely, obliquely, or parallel to a longitudinal axis or along the circumference of the dialyzer apparatus.

9. The system according to claim 7, in which the sensor device comprises a radiation measuring unit having a measurement optic unit having a focal depth and a focal direction, and having a light detector comprising a light-sensitive detector surface, wherein the measurement optic unit is designed to map a spatial region from the internal volume portion of the housing of the dialyzer apparatus on the detector surface of the light detector, with the mapped spatial region being defined by the focal depth and the focal direction and the focal depth and focal direction of the measurement optic unit is configured to be adjusted or selected before startup or during operation such that the spatial region to be mapped inside the internal volume portion is selectable.

10. The system according to claim 1, in which the sensor device comprises:

a radiation transmitting unit configured to emit a range of radiation; and a radiation measuring unit having at least one light detector and a wavelength selection unit with the wavelength selection unit being designed to select a narrow-band wavelength range including a reference wavelength range from the range of radiation emitted by the radiation transmitting unit, such that an optical interaction occurs with a selected material located during operation on or in the dialyzer apparatus or in the internal volume portion of the housing.

11. The system according to one of claim 1, wherein the sensor device is designed to detect at least one of:

in a blood region of the internal volume portion, the measurement of one or more parameters indicative of the concentration of one or more substances, in a dialysate region of the internal volume portion, the measurement of a parameter indicative of the concentration of one or more substances, or in the blood region, measurement of a parameter indicative of a physical property of the blood.

12. A sensor device comprising:

the sensor device of the system of claim 1, the sensor device comprising at least one sensor for detecting the at least one radiation signal from the internal volume portion of the housing, wherein the sensor device in its connected state to the dialyzer apparatus forms the system.

13. The sensor device according to claim 12 further comprising at least one radiation transmitter for transmitting radiation onto a surface of the housing of the dialyzer apparatus and/or into the internal volume portion of the dialyzer apparatus, wherein the sensor device is reusable.

14. The sensor device according to claim 12, wherein at least one of the following mechanisms is provided for the sensor device to be attachable in the detachable fashion on the housing:

the sensor device is embodied as a clip unit having at least one flexible clip arm or clip cuff wherein the at least one clip arm or clip cuff is configured to encompass the housing in an angular range of more than 180°;

the sensor device comprises a base body and a clip unit having at least one elastically flexible clip arm attached to the base body or articulated on the base body configured to at least partially encompass the housing, to enter into a fixed, removable connection therewith, or encompass the housing in a clip-like fashion;

the sensor device comprises a first member of the connector unit and the dialyzer apparatus comprises a second member of the connector unit, with the first member being designed to engage with the second member or with the second member being designed to engage with the first member in a removable positive fit;

the sensor device is clamped on the housing by an elastic clamping unit, with the clamping unit configured to encompass the sensor device and the housing of the dialyzer apparatus in its clamped state;

the sensor device comprises a base body and at least one arm or a pair of arms or cuffs articulated on the base body or connected to the base body in an elastically flexible fashion, each comprising a distal end region having a first member of a hook or engaging unit provided thereon, with the arm or the arms and/or cuffs being designed to encompass the housing in an angular range of more than 180°, and an elastically tensible clamping unit having at least one end section opposite one another, on each of which a second member of a hook or engaging unit is provided that is configured to detachably engage the first member of the hook or engaging unit, with each second member on the end section of the clamping unit being able to engage with the first member on the end regions of the arms and/or clamps of the sensor device; or the sensor device is designed to be integrated into a housing wall of the dialyzer apparatus in the removable fashion.

15. A dialyzer apparatus comprising:
the dialyzer apparatus of claim 1, the dialyzer apparatus configured such that the sensor device may be operatively connected to the dialyzer apparatus in a removable fashion and, in a connected state, forms the system;
wherein the sensor device comprises:
  at least one sensor for detecting the at least one radiation signal from the internal volume portion of the housing;
  at least one radiation transmitter for transmitting radiation onto the a surface and/or into the internal volume portion of the dialyzer apparatus, wherein the sensor device is reusable; or
  at least one of the following mechanisms for the sensor device to be attachable in the detachable fashion on the housing:
    the sensor device is embodied as a clip unit having at least one flexible clip arm or clip cuff wherein the at least one clip arm or clip cuff is configured to encompass the housing in an angular range of more than 180° ;
    the sensor device comprises a base body and a clip unit having at least one elastically flexible clip arm attached to the base body or articulated on the base body configured to at least partially encompass the housing, to enter into a fixed, removable connection therewith, or to encompass the housing in a clip-like fashion;
    the sensor device comprises a first member of a connector unit and the dialyzer apparatus comprises a second member of the connector unit, with the first member being designed to engage with the second member or with the second member being designed to engage with the first member in a removable positive fit;
    the sensor device is clamped on the housing by an elastic clamping unit, with the clamping unit configured to encompass the sensor device and the housing of the dialyzer apparatus in its clamped state;
    the sensor device comprises a base body and at least one arm or a pair of arms or cuffs articulated on the base body or connected to the base body in an elastically flexible fashion, each comprising a distal end region having a first member of a hook or engaging unit provided thereon, with the arm or the arms and/or cuffs being designed to encompass the housing in an angular range of more than 180° , and an elastically tensible clamping unit having at least one end section opposite one another, on each of which a second member of a hook or engaging unit is provided that is configured to detachably engage the first member of the hook or engaging unit, with each second member on the end section of the clamping unit being able to engage with the first member on the end regions of the arms and/or clamps of the sensor device; or
    the sensor device is designed to be integrated into tho a housing wall of the dialyzer apparatus in the removable fashion.

16. The dialyzer apparatus according to claim 15, having at least one of the following features:
  the housing comprises a housing wall having at least one window region that is permeable to the radiation;
  the membrane filter device configured for placement in the housing in a removable fashion;
  an interior housing removably fixed in the housing that encompasses the membrane filter device;
  the interior housing configured for removable insertion in the housing;
  the membrane filter device configured as a single-use article;
  the interior housing and the membrane filter device configured as a single-use article;
  the dialyzer apparatus as a whole configured as a single-use article;
  the internal volume portion comprises a dialysate region through which dialysate is able to flow during operation and a blood region through which blood is able to flow during operation, with the dialysate region being spatially separated from the blood region by the membrane filter unit;
  the membrane filter unit configured to allow a material exchange between the blood and the dialysate during operation driven by concentration gradients of materials dissolved in the blood and/or in the dialysate,
  the dialyzer apparatus configured as an intelligent dialyzer; or
  the dialyzer apparatus comprises interfaces to an external control unit.

17. A dialysis machine for conducting a dialysis treatment on a patient comprising a dialyzer apparatus according to claim 16 and the sensor device to form the system.

18. The dialysis machine according to claim 17, wherein the dialyzer apparatus comprises at least one housing holder that is embodied separately or connected in a fixed fashion to the dialysis machine and that is designed to be mechanically connected to the dialysis machine at least during operation and to fix the dialyzer apparatus in a removable fashion.

19. The dialysis machine according to claim 18, wherein the sensor device is integrated into the housing holder.

* * * * *